United States Patent
Abele et al.

(10) Patent No.: US 9,296,673 B2
(45) Date of Patent: Mar. 29, 2016

(54) PREPARATION OF BICYCLO[2.2.2]OCTAN-2-ONE COMPOUNDS

(75) Inventors: Stefan Abele, Allschwil (CH); Jacques-Alexis Funel, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 179 days.

(21) Appl. No.: 13/880,520

(22) PCT Filed: Oct. 19, 2011

(86) PCT No.: PCT/IB2011/054660
§ 371 (c)(1),
(2), (4) Date: Apr. 19, 2013

(87) PCT Pub. No.: WO2012/052939
PCT Pub. Date: Apr. 26, 2012

(65) Prior Publication Data
US 2013/0211104 A1 Aug. 15, 2013

(30) Foreign Application Priority Data
Oct. 20, 2010 (WO) .................. PCT/IB2010/054747

(51) Int. Cl.
| | |
|---|---|
| C07C 309/00 | (2006.01) |
| C07C 45/00 | (2006.01) |
| C07C 45/67 | (2006.01) |
| C07C 29/147 | (2006.01) |
| C07C 45/30 | (2006.01) |
| C07C 45/59 | (2006.01) |
| C07C 45/66 | (2006.01) |
| C07C 45/81 | (2006.01) |
| C07C 67/313 | (2006.01) |
| C07C 309/66 | (2006.01) |
| C07D 317/72 | (2006.01) |
| C07C 45/29 | (2006.01) |

(52) U.S. Cl.
CPC .............. *C07C 45/67* (2013.01); *C07C 29/147* (2013.01); *C07C 45/29* (2013.01); *C07C 45/30* (2013.01); *C07C 45/59* (2013.01); *C07C 45/66* (2013.01); *C07C 45/81* (2013.01); *C07C 67/313* (2013.01); *C07C 309/66* (2013.01); *C07D 317/72* (2013.01); *C07C 2101/14* (2013.01); *C07C 2102/44* (2013.01)

(58) Field of Classification Search
CPC ........ C07C 45/64; C07C 45/81; C07C 45/66; C07C 45/72; C07C 309/25; C07C 309/66
USPC .......................................... 558/44; 568/313
See application file for complete search history.

(56) References Cited

U.S. PATENT DOCUMENTS

| | | | |
|---|---|---|---|
| 8,202,885 B2 | 6/2012 | Hilpert et al. | |
| 8,816,118 B2 | 8/2014 | Abele et al. | |
| 2011/0039905 A1 | 2/2011 | Hubler et al. | |
| 2013/0289295 A1 | 10/2013 | Abele et al. | |

FOREIGN PATENT DOCUMENTS

EP 0 053823 4/1985

OTHER PUBLICATIONS

Bella et al, Synergic asymmetric organocatalysis (SAOc) of Cinchona alkaloids and secondary amines in the synthesis of bicyclo[2.2.2]octan-2-ones, Chem. Commun. (2009) pp. 597-599.*
Nagata, W., et al., "Synthesis of Bridged Steroids. III. [1] Cholestane Derivatives Having a Bridged Bicyclo[2.2.2]Octane Ring System of Atisine Type", Chem. Pharm. Bull. vol. 16, No. 5, pp. 885-896, (1968).
Di Stefano, S., et al., "Elusive 6-exo-Hydroxybicyclo[2.2.2]octan-2-ones from the Corresponding Acetates by Methanolysis in the Presence of $CH_3ONa/La(OTf)_3$", Organic Letters, vol. 4, No. 16, pp. 2783-2785, (2002).
Arai, T., et al., "A New Multifunctional Heterobimetallic Asymmetric Catalyst for Michael Additions and Tandem Michael-Aldol Reactions", Agnew. Chem. Int. Ed. Engl., (1996), vol. 35, No. 1, pp. 104-106.
Bella, M., et al., "Synergic Asymmetric Organocatalysis (SAOc) of Cinchona Alkaloids and Secondary Amines in the Synthesis of Bicyclo[2.2.2]Octan-2-Ones", Chem. Commun., (2009), pp. 597-599, doi:10.1039/b816550e.
Defieber, C., et al., "Chiral Olefins as Steering Ligands in Asymmetric Catalysis", Agnew. Chem. Int. Ed., (2008), vol. 47, pp. 4482-4502, doi:10.1002/anie.200703612.
De Santis, B., et al., "On the Diastereoselectivity of the Aqueous-Acid-Catalyzed Intramolecular Aldol Condensation of Oxocyclohexaneacetaldehydes", Helvetica Chimica Acta, vol. 81, (1998), pp. 2375-2387.

(Continued)

*Primary Examiner* — Andrew D Kosar
*Assistant Examiner* — Raymond Covington
(74) *Attorney, Agent, or Firm* — Hoxie & Associates LLC

(57) ABSTRACT

The present invention relates to a new process for the preparation of 6-hydroxy-5-arylbicyclo[2.2.2]octan-2-one compounds of the formula (II); which may subsequently be further transformed to compounds of the formula (I):

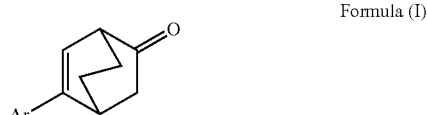

Formula (I)

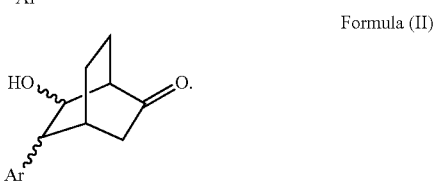

Formula (II)

The present invention further relates to novel compounds as such, which compounds are useful intermediates in the above process.

18 Claims, No Drawings

(56) References Cited

OTHER PUBLICATIONS

Funel, J.-A., et al., "Design and Scale-Up of Diels-Alder Reactions for the Practical Synthesis of 5-Phenylbicyclo[2.2.2]oct-5-en-2-one", Org. Process. Res. Dev., (2011), vol. 15, pp. 1420-1427, dx.doi.org/10.1021/op200139r.

Greene, T., "Protective Groups in Organic Synthesis", 3rd Edition, front cover and Table of Contents, (Wiley-Interscience), (1999).

Hill, R. K., et al., "Synthesis and Chiroptical Properties of 5,7-Dioxobicyclo[2.2.2]oct-2-ene and Bicyclo[2.2.2]octaine-2,5-dione", J. Org. Chem., (1985), vol. 50, pp. 5528-5533.

Jiricek, J., et al., "Enantioselective Synthesis of (−)-Gilbertine via a Cationic Cascade of Cyclization", J. Am. Chem., Soc., (2004), vol. 126, pp. 3534-3538, doi:10.1021/ja0399021.

Johansson, C.C.C., et al., "Metal Catalyzed α-Arylation of Carbonyl and Related Molecules: Novel Trends in C—C Bond Formation by C—H Bond Functionalization", Agnew. Chem. Int. Ed., (2010), vol. 49, pp. 676-707, doi:10.1002/aniew.200903424.

Jørgensen, M., et al., "Efficient Synthesis of α-Aryl Esters by Room-Temperature Palladium-Catalyzed Coupling of Aryl Halides with Ester Enolates", J. Am. Chem. Soc., (2002), vol. 124, pp. 12557-12565, doi:10.1021/ja027643u.

Kinoshita, T., et al., "Syntheses and Racemization via Intermolecular Prototropy of Optically Active Alkyltropylium Ions. A Novel Scale for the Kinetic Brønsted Basicity of Organic Solvents", Tetrahedron Letters, vol. 31, No. 28, pp. 4057-4060, (1990).

Luo, Y., et al, "A Practical Chemo-enzymatic Synthesis of Homochiral Bicyclo[2.2.2]octane-2,5-dione", J. Org. Chem., (2010), vol. 75, pp. 2057-2060, (Published on Web Feb. 12, 2010), doi:10.1021/jo9023705.

Mori, K., et al., "Diterpenoid Total Synthesis—XIX[i] (±)-Steviol and Erythroxydiol A: Rearrangements in Bicyclooctane Compounds", Tetrahedron, vol. 28, pp. 3217-3226, (1972).

Ohshima, T., et al., "Enantioselective Total Synthesis of (−)-Strychnine: Development of A Highly Practical Catalytic Asymmetric Carbon—Carbon Bond Formation and Domino Cyclization", vol. 60, (2004) pp. 9569-9588, doi:10.1016/j.tet.2004.06.141.

Perry, R. H., et al., "Perry's Chemical Engineer's Handbook, 7th Edition", McGraw-Hill, (1997), (front cover and table of contents).

Schmoldt, P., et al,. "A Versatile Synthesis of Bicyclo [2.2.2]octan-2-one Derivatives", Agnew. Chem. Int. Ed. Engl. (1996), vol. 35, No. 1, pp. 1071-1078.

Shintani, R., et al., "Chiral Diene Ligands for Asymmetric Catalysis", Aldrichimica Acta, vol. 42, No. 2, (2009), pp. 31-38.

Strzalko, T., et al., "1,2- vs 1,4-Regioselectivity of Lithiated Phenylacetonitrile Toward α, β-Unsaturated Carbonyl Compounds. 2 Relation Between the Regioselectivity and the Structure of the Species in Solution", J. Org. Chem., (1998), vol. 63, pp. 3295-3301, (published on Web May 15, 1998).

Tokunaga, N., et al., "$C_2$-Symmetric Bicyclo[2.2.2]octadienes as Chiral Ligands: Their High Performance in Rhodium-Catalyzed Asymmetric Arylation of N-Tosyarylimines", J. Am. Chem. Soc., (2004), vol. 126, pp. 13584-13585, doi:10.1021/ja044790e.

Tzvetkov, N. T., et al., "Synthesis of Optically Active (1R, 4S, 6S)-6-hydroxybicyclo[2.2.2]octan-2-one", Tetrahedron: Asymmetry, vol. 17, (2006), pp. 993-998, doi:10.1016/j.tetasy_2006.03.013.

Wascholowski, V., et al., "A General Organocatalytic Enantioselective Malonate Addition to α,β-Unsaturated Enones", Chem. Eur. J., (2008), vol. 14, pp. 6155-6165, doi:10.1002/chem.200800673.

Werstiuk, N. H., et al., "Synthesis of Bicyclic Diones and Thiones. Facile Methylation of the Enolates of Bicyclo [2.2.1]heptane-2,5-dione and bicyclo[2.2.2]octane-2,5-dione. An AMI Computational Study of Bicyclic Enolates", Can. J. Chem., vol. 70, pp. 974-980, (1992).

\* cited by examiner

PREPARATION OF BICYCLO[2.2.2]OCTAN-2-ONE COMPOUNDS

CROSS REFERENCE TO RELATED APPLICATIONS

This application is a United States National Stage Application under 35 U.S.C. 371 of PCT Application No. PCT/IB2011/054660, filed on Oct. 19, 2011, which claims the benefit of PCT Application No. PCT/IB2010/054747, filed Oct. 20, 2010.

FIELD OF THE INVENTION

The present invention relates to a new process for the preparation of 6-hydroxy-5-arylbicyclo[2.2.2]octan-2-one compounds of the formula (II); which may subsequently be further transformed to compounds of the formula (I):

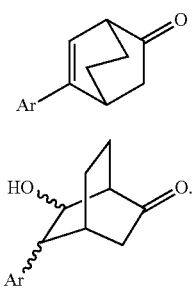

Formula (I)

Formula (II)

The present invention further relates to novel compounds of formula 2, formula 3 and formula 4 as such. The present compounds of formula 2, formula 3 and formula 4 can be used as intermediates in the preparation of compounds of the formula (II). The present invention further relates to novel compounds of formula 6 as such. The present compounds of formula 6 can be used as intermediates in the preparation of 5-aryl-bicyclo[2.2.2]oct-5-en-2-one compounds of the formula (I). Said compounds of the formula (I) are key building blocks in the synthesis of certain calcium channel blockers described in WO2008/132679 and WO2009/130679. Especially, they can be further transformed to the compound isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester, or the corresponding (1S,2S,4S)-stereoisomer thereof.

Furthermore, compounds of formula (I) can be used for the synthesis of bicyclic dienes of formula (III) (especially in enantiomerically enriched form)

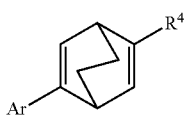

Formula (III)

wherein $R^4$ represents any group which may be introduced by an organometallic reagent; especially alkyl or aryl. Compounds of formula (III), especially $C_2$-symmetrical 2,5-disubstituted bicyclo[2.2.2]octa-2,5-dienes (bod*), are rapidly gaining considerable interest as chiral ligands in asymmetric catalysis, see for example: E. Carreira et al., *Angew. Chem.* *Int. Ed.* 2008, 47, 2-23; T. Hayashi et al., *Aldrichim. Acta.* 2009, 42, 31. The current syntheses generally suffer from very low yields.

Compounds of formula (II) are known in literature (M. Bella, D. M. Schietroma, P. P. Cusella, T. Gasperi, V. Visca, *Chem. Commun.* 2009, 597-599), however, the described synthesis uses a Tandem Michael addition-aldol cyclization catalyzed by various proline or cysteine derived catalysts in the presence of cinchona alkaloid derivatives as chiral additives. The method produces a mixture of diastereomers which were separated by chromatography; and the obtained enantioselectivities are modest (highest ee is 87%). Further, this publication does not describe the further transformation of the compounds of formula (II) into compounds of formula (I).

Compounds of formula (I) are known from literature (K. Takeuchi et al., *Tetrahedron Letters* 1990, 31, 4057-4060), however they are commonly synthesized in multi-step reactions using in the key step a Diels Alder reaction of either 2-(trimethylsiloxy)-1,3-cyclohexadiene with alpha-chloroacrylonitrile (Funel, J.-A.; Schmidt, G.; Abele, S. *Org. Process Res. Dev.* Publication Date (Web): Jun. 27, 2011; A. J. Carnell et al., *J. Org. Chem.* 2010, 75, 2057-2060) or with alpha-acetoxyacrylonitrile (N. H. Werstuik et al., *Can. J. Chem.* 1992, 70, 974-980 and WO2008/132679; WO2009/130679); or a Diels-Alder reaction of hydrochinone and maleic anhydride (L. A. Paquette et al., *J. Org. Chem.* 1985, 50, 5528-5533). These methods generally have the racemic bicyclo[2.2.2]octane-2,5-dione as intermediate and generally suffer from very low yield, use expensive and toxic starting materials and/or are not robust for scale up.

In addition, the cyclization of a compound of structure 4 leading to compounds of structure (II):

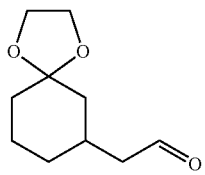

Structure 4

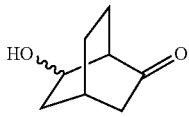

Structure (II)

wherein no aryl substituent is present in these compounds, is known in the literature (for example K. Mori et al., *Tetrahedron* 1972, 28, 3217; M. Bettolo et al., *Helv. Chim. Acta* 1998, 81, 2375; J. Mattay et al., *Synthesis* 2003, 1071-1078; J. Mattay et al., *Tetrahedron: Asymmetry* 2006, 993).

It has now surprisingly been found that such cyclization can be performed even in presence of a large substituent in the aldehyde side chain of compounds of structure 4, i.e. an aryl substituent in alpha-position to the aldehyde function. In addition, the process of the present invention is scalable and can be performed under surprisingly mild conditions, and is higher yielding while less unit operations are needed when compared to the above cited literature. Furthermore, the process leads to the compounds of formula (II) in unpredictably high diastereoisomeric excess; and in high enantiomeric excess when stereoisomerically enriched starting materials are used. The starting material for said cyclization, in turn, is available in a surprisingly convenient and scalable multistep reaction, which comprises, as a key step, a transition metal catalyzed alpha-arylation reaction. In addition, the process may be extended by a two-step reaction, which comprises, as a key step, a surprisingly mild and scalable elimination reaction, to obtain useful building blocks of formula (I), optionally in enantiomerically enriched form.

DESCRIPTION OF THE INVENTION

1) In a first embodiment, the invention relates to a process for the synthesis of 6-hydroxy-5-arylbicyclo[2.2.2]octan-2-one compounds, the compounds of the formula (II):

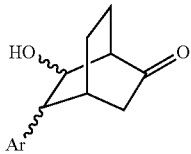

Formula (II)

said process comprising a cyclization of a compound of formula 4 (preferred sub-embodiment), or of a compound of formula 10 (less preferred sub-embodiment):

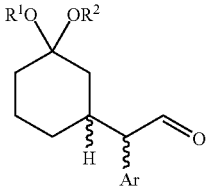

Formula 4

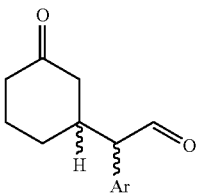

Formula 10 wherein
Ar represents an aryl group; and
—OR¹ and —OR², together with the carbon atom to which they are attached to, represent a ketal group.

2) Another embodiment relates to the process according to embodiment 1), wherein said process comprises a cyclization of a compound of formula 4 to a compound of formula (II); wherein the compound of formula (II) is formed in the reaction mixture in diastereomerically enriched form; wherein the major diastereoisomer is (1R*,4R*,5S*,6S*)-6-hydroxy-5-arylbicyclo[2.2.2]octan-2-one:

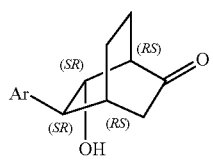

i.e. the compound of formula (II) wherein the relative configuration is as in the compounds of formula (IIa) or formula (IIb) below:

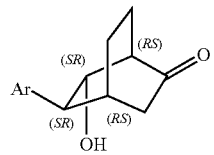

Formula (IIa)

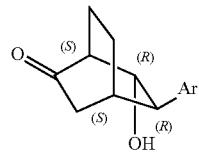

Formula (IIb)

wherein preferably the diastereomeric purity is greater than about 70%, notably greater than 80%, especially greater 90%.

The major diastereoisomer is (1R*,4R*,5S*,6S*)-6-hydroxy-5-arylbicyclo[2.2.2]octan-2-one, whereas the possible minor diastereisomers are (1R*,4R*,5R*,6R*)-6-hydroxy-5-arylbicyclo[2.2.2]octan-2-one, (1R*,4R*,5R*,6S*)-6-hydroxy-5-arylbicyclo[2.2.2]octan-2-one, and (1R*,4R*,5S*,6R*)-6-hydroxy-5-arylbicyclo[2.2.2]octan-2-one.

3) Another aspect of the present invention relates to the process according to embodiments 1) or 2), wherein the compound of formula 4 (preferred sub-embodiment), or the compound of formula 10 (less preferred sub-embodiment) is cyclized;
preferably at a reaction temperature of about 20-75° C. (notably at about 45-70° C., especially at about 50° C.);
wherein said cyclization is performed in presence of:
  an aqueous mineral acid (notably aqu. HCl, especially about 32% aqu. HCl); preferably in an amount of about 0.1-2 equ. (notably about 0.1-1 equ., especially about 0.3 equ.) per equ. of the compound of formula 4 or 10; and
  a solvent (especially a solvent selected from the group consisting of aromatic solvents (such as toluene or benzene), esters (such as EtOAc or iPrOAc), alcohols (such as methanol, ethanol, isopropanol), ethers (such as THF, 2-methyltetrahydrofurane, 1,4-dioxane or tert-butylmethylether), ketones (such as acetone), chlorinated hydrocarbons (such as DCM), or acetonitrile; notably ethylacetate); wherein said solvent is present in an amount of about 1-10 vol. (notably 1-5 vol., especially about 1-2 vol.) with respect to the compound of formula 4 or 10; and
wherein said compound of formula (II) is isolated from the reaction mixture by solid-liquid separation.

4) Another embodiment relates to the process according to embodiment 3), wherein said isolation from the reaction mixture by solid-liquid separation is achieved
  by solid-liquid separation (especially filtration) of the precipitated product at the reaction temperature;
  or by
    1. cooling of the reaction mixture to a temperature below the reaction temperature, and
    2. solid-liquid separation (especially filtration) of the precipitated product.

The process of embodiments 3) and 4), wherein the product is isolated by solid-liquid separation (especially filtration) is a diastereoselective process. It usually leads to isolated (1R*,4R*,5S*,6S*)-6-hydroxy-5-arylbicyclo[2.2.2]octan-2-one compounds in diastereomeric purity (with respect to the possible minor diastereisomers (1R*,4R*,5R*,6R*)-6-hydroxy-5-arylbicyclo[2.2.2]octan-2-one, (1R*,4R*,5R*,6S*)-6-hydroxy-5-arylbicyclo[2.2.2]octan-2-one, and (1R*,4R*,5S*,6R*)-6-hydroxy-5-arylbicyclo[2.2.2]octan-2-one) of greater than 90%, notably greater than 95%, especially greater than 99%. In a particular embodiment, essentially pure diastereoisomers of the compounds of formula (II): (1R*,4R*,5S*,6S*)-6-hydroxy-5-arylbicyclo[2.2.2]octan-2-one, are isolated.

5) Another embodiment relates to the process according to any one of embodiments 1) to 4), wherein said compound of formula 4, or said compound of formula 10, is obtained from a compound of formula 2:

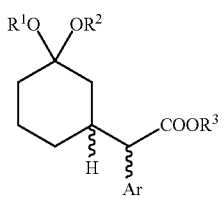

Formula 2 wherein
Ar represents an aryl group;
—OR$^1$ and —OR$^2$, together with the carbon atom to which they are attached to, represent a ketal group; and
—COOR$^3$ represents an ester group.

6) Another embodiment relates to the process according to any one of embodiments 1) to 5), wherein, in case said process comprises a cyclization of a compound of formula 4, said compound of formula 4 is obtained from said compound of formula 2
- via a direct reduction of the ester group —COOR$^3$, or, preferably,
- via a sequence of reaction steps comprising first a reduction of the ester group —COOR$^3$ of the compound of formula 2 to the corresponding alcohol of formula 3:

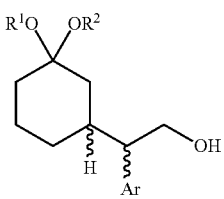

Formula 3 and a subsequent oxidation of said alcohol.

7) Another embodiment relates to the process according to embodiment 5), wherein, in case said process comprises a cyclization of a compound of formula 10, said compound of formula 10 is obtained from a compound of formula 2 via
A) a sequence of the following steps:
1. reduction of the ester group —COOR$^3$ of the compound of formula 2 to the corresponding alcohol;
2. deprotection of the ketal protecting group; and
3. subsequent oxidation of the alcohol group obtained in step 1;
to obtain the compound of formula 10; or
B) a sequence of the following steps:
1. deprotection of the ketal protecting group of the compound of formula 2;
2. simultaneous reduction of the ester group —COOR$^3$, and the ketone obtained in step 1, to the respective alcohols; and
3. subsequent simultaneous oxidation of both alcohol groups obtained in step 2;
to obtain the compound of formula 10.

8) Another embodiment relates to the process according to embodiment 7), wherein, in sequence A), said reduction of the ester group —COOR$^3$ of the compound of formula 2 to the corresponding alcohol, followed by said deprotection of the ketal protecting group, leads to a compound of formula 11:

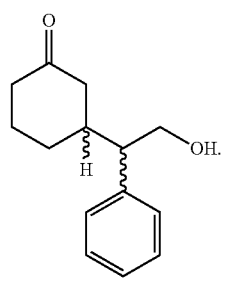

Formula 11

9) Another embodiment relates to the process according to embodiment 7), wherein, in sequence B), said deprotection of the ketal protecting group of the compound of formula 2 leads to a compound of formula 8:

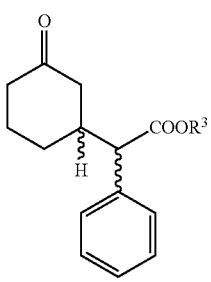

Formula 8 and said simultaneous reduction of the ester group —COOR$^3$, and of the ketone obtained in step 1, leads to a compound of formula 9:

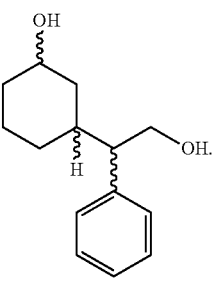

Formula 9

10) Another embodiment relates to the process according to any one of embodiments 1) to 9), wherein, in case said process comprises a cyclization of a compound of formula 4, said compound of formula 4, is obtained from a compound of formula 13.

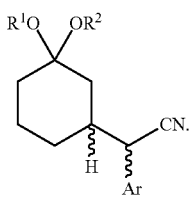

Formula 13

11) Another embodiment relates to the process for the synthesis of a compound of the formula (II):

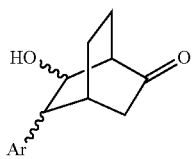

Formula (II)

according to any one of embodiments 1) to 6), said process comprising a cyclization of a compound of formula 4:

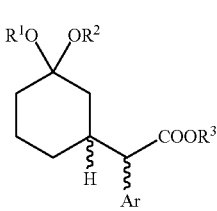

Formula 4 wherein said compound of formula 4 is obtained from a compound of formula 2:

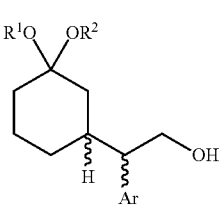

Formula 2 via a sequence of reaction steps comprising first a reduction of the ester group —COOR$^3$ of the compound of formula 2 to the corresponding alcohol of formula 3:

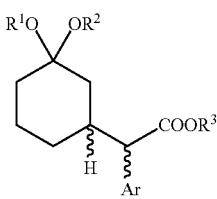

Formula 3 and a subsequent oxidation of said alcohol.

12) Another embodiment relates to the process according to any one of embodiments 1) to 11), wherein said compound of formula 4, or said compound of formula 10, is used in situ (i.e. is not isolated) for said cyclization.

13) Another embodiment relates to the process according to any one of embodiments 5) to 12); wherein said compound of formula 2:

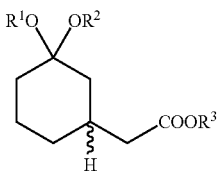

Formula 2 is obtained by a transition metal-catalyzed alpha-arylation of a carbonyl-containing compound of formula 1:

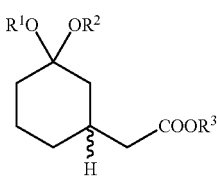

Formula 1 wherein
Ar represents an aryl group;
—OR$^1$ and —OR$^2$, together with the carbon atom to which they are attached to, represent a ketal group; and
—COOR$^3$ represents an ester group.

14) A further aspect of the present invention relates to a process according to embodiment 13), wherein said compound of the formula 1:

Formula 1 is obtained by a sequence of reaction steps comprising a step wherein cyclohex-2-enone is coupled with a malonic acid di-ester, wherein said malonic acid di-ester has the formula R$^{31}$OOC—CH$_2$—COOR$^{31}$; wherein —COOR$^{31}$ represents an ester group.

15) Another embodiment relates to the process according to embodiments 13) or 14), wherein R$^3$ is methyl. In a sub-embodiment according to embodiment 14), in case R$^{31}$ is different from R$^3$ (which especially is methyl), said ester —COOR$^{31}$ is, in a first step, transformed into an ester —COOR$^3$, wherein R$^3$ is especially methyl.

16) Another embodiment relates to the process according to embodiments 14) or 15), wherein said coupling step is effected under the conditions published in literature by Shibasaki et al. (T. Aria, H. Sasai, K.-I. Aoe, K. Okamura, T. Date, M. Shibasaki, *Angew. Chem. Int. Ed.* 1996, 35, 104-106; T. Ohshima, Y. Xu, R. Takita, M. Shibasaki, *Tetrahedron* 2004, 60, 9569-9588).

17) Another embodiment relates to the process according to embodiment 14) to 16), wherein the compound of formula 14:

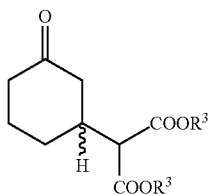

Formula 14 is the product of said coupling step.

18) Another embodiment relates to the process according to embodiment 17), wherein the compound of formula 14 is further transformed to a compound of formula 15:

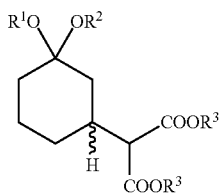

Formula 15 which in turn is decarboxylated to provide the compound of formula 1.

19) Another embodiment relates to the process according to embodiment 13), wherein the compound of formula 1 is obtained from a compound of formula 15:

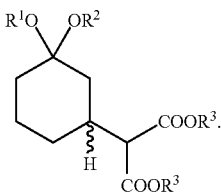

Formula 15

20) Another embodiment relates to the process according to embodiments 18) or 19), wherein the compound of formula 15 is decarboxylated at a temperature of about 120-150° C., especially about 135-145° C., particularly about 140° C.; wherein the reaction mixture comprises:
- an alkali metal halide in an amount of about 2-5 equ. per equ. of the compound of formula 15 (especially about 2 equ. of LiCl);
- water in an amount of about 1-2 equ. (especially about 1 equ.) per equ. of the compound of formula 15; and
- a polar aprotic solvent selected from DMSO, DMF, N-methylpyrrolidinone and dimethylacetamide (especially dimethylacetamide).

21) Another embodiment relates to the process according to any one of embodiments 14) to 20), wherein the compound of formula 1 (and, respectively, the compounds of formula 14 and 15) is obtained in enantiomerically enriched form. Respectively, embodiment 21) relates to the process of embodiment 13), wherein the compound of formula 1 is used in enantiomerically enriched form.

22) Another embodiment relates to the process of any one of embodiments 1) to 21), wherein the compound of formula 4 is used as a mixture of enantiomerically enriched diastereoisomers; preferably as a mixture of enantiomerically essentially pure diastereoisomers.

For avoidance of any doubt, embodiment 22) especially relates to the process of any one of embodiments 1) to 21), wherein the mixture of enantiomerically enriched diastereoisomers of the compound of formula 4a) is obtained from a mixture of enantiomerically enriched diastereoisomers of the compound of formula 2a) which in turn is obtained from the enantiomerically enriched compound of formula 1a); or the mixture of enantiomerically enriched diastereoisomers of the compound of formula 4b) is obtained from a mixture of enantiomerically enriched diastereoisomers of the compound of formula 2b) which in turn is obtained from the enantiomerically enriched compound of formula 1b):

Formula 1a)

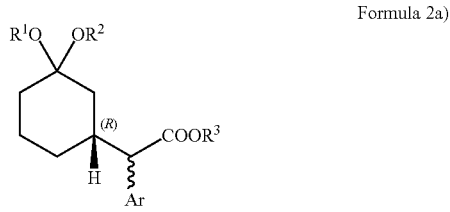

Formula 2a)

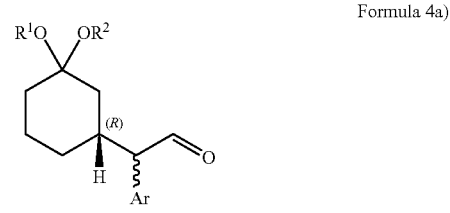

Formula 4a)

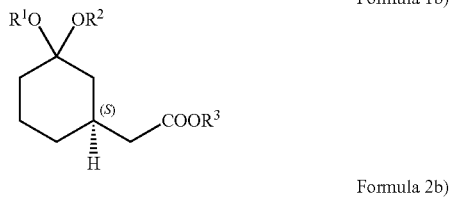

Formula 1b)

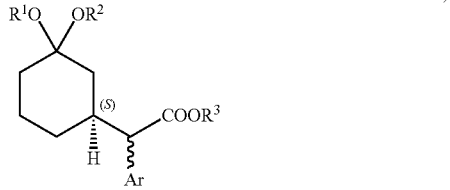

Formula 2b)

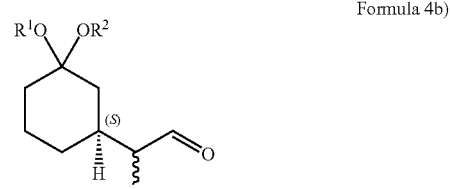

Formula 4b)

it being understood that according to embodiment 22) the enantiomerically enriched compound of formula (IIa) is obtained from the cyclization of the compound of formula 4a), respectively, the enantiomerically enriched compound of formula (IIb) is obtained from cyclization of the compound of formula 4b):

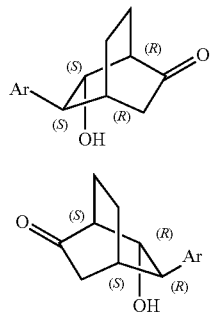

Formula (IIa)

Formula (IIb)

wherein the process encompasses mutatis mutandis the details given in embodiments 1) to 21).

23) Another embodiment relates to the process of any one of embodiments 5) to 9), 11) or 12); wherein the compound of formula 2

Formula 2

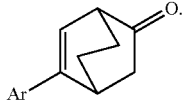

is obtained via a sequence of reaction steps comprising a step wherein cyclohex-2-enone is coupled with a 2-aryl malonic acid di-ester, wherein said 2-aryl malonic acid di-ester has the formula $R^{31}OOC$—$CHAr$—$COOR^{31}$.

24) Another embodiment relates to the process according to embodiment 23), wherein $R^3$ is methyl. In a sub-embodiment according to embodiment 23), in case $R^{31}$ is different from $R^3$ (which especially is methyl), said ester —$COOR^{31}$ is, in a first step, transformed into an ester —$COOR^3$, wherein $R^3$ is especially methyl.

25) Another embodiment relates to the process according to embodiments 23) or 24), wherein the compound of formula 16:

Formula 16 is the product of said coupling step.

26) Another embodiment relates to the process according to any one of embodiments 23) to 25), wherein said coupling step is effected under the conditions published in literature by Shibasaki et al. (M. Shibasaki et al., *Angew. Chem. Int. Ed.* 1996, 35, 104-106; M. Shibasaki et al., *Tetrahedron* 2004, 60, 9569-9588) to obtain compounds of Formula 16 below in enantiomerically enriched form.

27) Another embodiment relates to the process according to embodiments 25) or 26), wherein the compound of formula 16 is further transformed to a compound of formula 17:

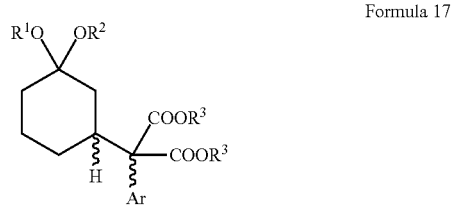

Formula 17 which in turn is decarboxylated to provide the compound of formula 2.

28) A further aspect of the present invention relates to a process according to any one of embodiments 1) to 27), wherein the compound of the formula (II) is further transformed to a compound the formula (I):

Formula (I)

29) Another embodiment relates to the process according to embodiment 28), wherein said transformation of the compound of the formula (II) to the compound of the formula (I) is effected via an elimination step.

30) Another embodiment relates to the process according to embodiment 29), wherein said elimination step comprises the activation of the alcohol function of the compound of formula (II).

31) Another embodiment relates to the process according to embodiments 29) or 30), wherein the compound of formula 6:

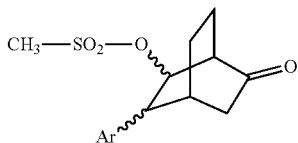

Formula 6 is an intermediate of said elimination step.

In a preferred sub-embodiment, said compound of formula 6 is in diastereomerically enriched form having the relative configuration (1S*,2R*,3R*,4S*) [i.e. the compound is (1S*, 2R*,3R*,4S*)-6-oxo-3-arylbicyclo[2.2.2]octan-2-yl methanesulfonate]:

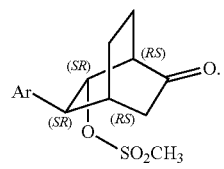

In a further preferred sub-embodiment, said diastereoisomer notably is enantiomerically enriched (preferably enantiomerically essentially pure), i.e. having either the absolute configuration (1R,2S,3S,4R) or (1S,2R,3R,4S).

32) Another embodiment relates to the process of any one of embodiments 28) to 31), wherein the compound of formula (I) is obtained as the enantiomerically enriched (R,R)-, respectively, (S,S)-isomer of the compound of formula (I):

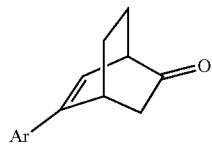
(R,R)-Formula (I)

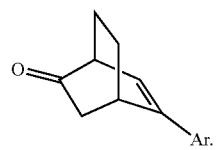
(S,S)-Formula (I)

For avoidance of any doubt, embodiment 32) especially relates to the process of embodiment 22).

33) Another embodiment relates to the process of any one of embodiments 28) to 31), wherein the compound of formula (I) is obtained in racemic form, or as mixture of enantiomers of any ratio; and wherein the enantiomerically enriched (R,R)-, respectively, (S,S)-isomer of the compound of formula (I):

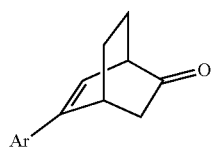
(R,R)-Formula (I)

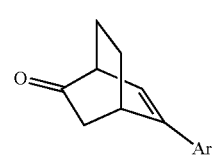
(S,S)-Formula (I)

is obtained by subsequent separation of the enantiomers using preparative chiral HPLC.

34) Another embodiment relates to the process for the synthesis of a compound of the formula (I):

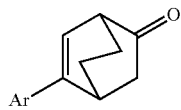
Formula (I)

wherein said compound of formula (I) is obtained from a compound of formula (II) according to any one of embodiments 28) to 33);
wherein said compound of formula (II) is obtained from a compound of formula 4 according to any one of embodiments 1) to 4), 11), 12), or 22);
wherein said compound of formula 4 is obtained from a compound of formula 2 according to any one of embodiments 5) or 6); and
wherein said compound of formula 2 is obtained from a compound of formula 1 according to any one of embodiments 14) to 21).

35) A further aspect of the present invention relates to a process according to any one of embodiments 28) to 34), wherein the compound of the formula (I) is further transformed to a compound the formula (III):

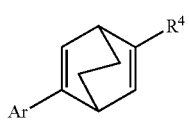
Formula (III)

wherein $R^4$ represents any group which may be introduced by an organometallic reagent (especially organolithium, organomagnesium, or organoboron reagent); especially $R^4$ represents alkyl or aryl. In a sub-embodiment said transformation is effected either by a sequence of direct addition and elimination; or by the coupling of said organometallic reagent with the respective enol trifluoromethanesulfonate of formula 18

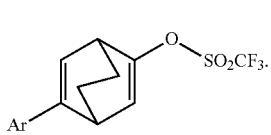
Formula 18

36) Another embodiment relates to the process according to embodiment 35), wherein said transformation is effected via an addition-elimination sequence.

37) Another embodiment relates to the process according to embodiment 36), wherein compound of formula 19 is an intermediate in said addition-elimination sequence:

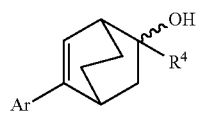
Formula 19 wherein said compound of formula 19 is obtained by an addition reaction of said organometallic reagent to the ketone of the compound of formula (I).

38) Another embodiment relates to the process according to any one of embodiments 36) to 37), wherein $R^4$ is different from Ar; i.e. compound of formula (III) is not $C_2$-symmetrical:

39) Another embodiment relates to the process of any one of embodiments 35) to 38), wherein the compound of formula (III) is obtained in form of the enantiomerically enriched (R,R)-, respectively, (S,S)-isomer of the compound of formula (III):

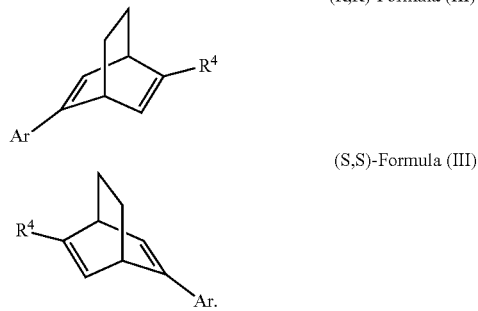

(R,R)-Formula (III)

(S,S)-Formula (III)

40) A further aspect of the present invention relates to novel compounds of the formula 4:

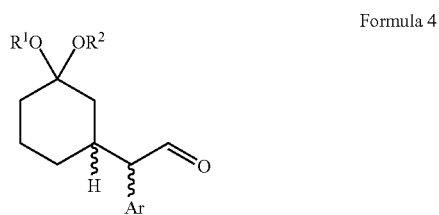

Formula 4 wherein
Ar represents an aryl group; and
—$OR^1$ and —$OR^2$, together with the carbon atom to which they are attached to, represent a ketal group.

These compounds are key intermediates, particularly in the process of embodiments 1) to 4), 11) and 22).

41) A further aspect of the present invention relates to novel compounds of the formula 3:

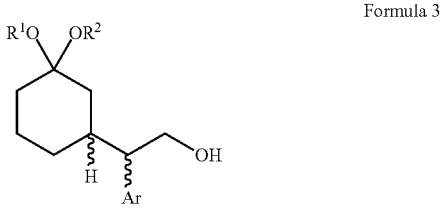

Formula 3 wherein
Ar represents an aryl group; and
—$OR^1$ and —$OR^2$, together with the carbon atom to which they are attached to, represent a ketal group.

These compounds are intermediates, particularly in the process of embodiment 6), 11) and 22).

42) A further aspect of the present invention relates to novel compounds of the formula 2:

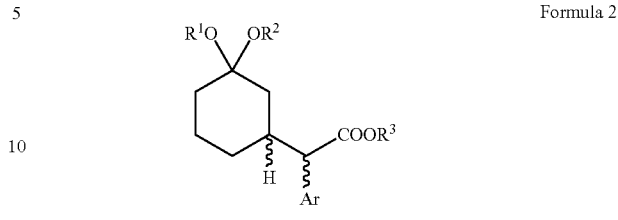

Formula 2 wherein
Ar represents an aryl group;
—$OR^1$ and —$OR^2$, together with the carbon atom to which they are attached to, represent a ketal group; and
—$COOR^3$ represents an ester group.

These compounds are intermediates, particularly in the process of embodiment 5), 11) and 22).

43) A further aspect of the present invention relates to novel compounds of the formula 6:

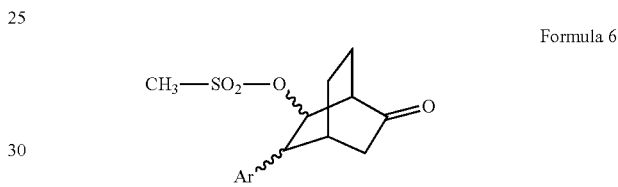

Formula 6 wherein
Ar represents an aryl group.

These compounds are intermediates, particularly in the process of embodiment 31) to 34).

44) A further aspect of the present invention relates to the compound of any one of embodiments 40) to 42), wherein said compound is in form of a mixture of diastereoisomers, wherein each diastereoisomer is in enantiomerically enriched form (preferably enantiomerically essentially pure). For avoidance of any doubt, one stereocenter is in enantiomerically enriched (preferably enantiomerically pure) absolute configuration as depicted in the respective formulae 2a), 4a) and, mutatis mutandis, 3a); or in formulae 2b), 4b) and, mutatis mutandis, 3b); whereas the other stereocenter is not controlled giving rise to said mixture of diastereoisomers.

45) A further aspect of the present invention relates to the compound of embodiment 43), wherein said compound of formula 6 is in diastereomerically enriched form having the relative configuration (1S*,2R*,3R*,4S*) [i.e. the compound is (1S*,2R*,3R*,4S*)-6-oxo-3-arylbicyclo[2.2.2]octan-2-yl methanesulfonate]:

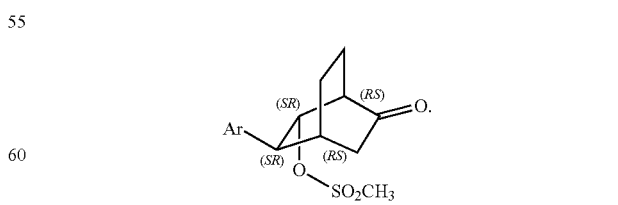

In a sub-embodiment, said diastereoisomer notably is enantiomerically enriched (preferably enantiomerically essentially pure), i.e. having either the absolute configuration (1R,2S,3S,4R) or (1S,2R,3R,4S).

46) Another embodiment relates to the compounds of formula 4 according to embodiment 40), selected from the group consisting of:
2-Phenyl-2-((R)-1,4-dioxaspiro[4.5]decan-7-yl)-acetaldehyde; and
2-Phenyl-2-(1,4-dioxaspiro[4.5]decan-7-yl)acetaldehyde.

47) Another embodiment relates to the compounds of formula 3 according to embodiment 41), selected from the group consisting of:
2-Phenyl-2-((R)-1,4-dioxaspiro[4.5]decan-7-yl)-ethanol;
2-Phenyl-2-(1,4-dioxaspiro[4.5]decan-7-yl)ethanol;
rac-(R*)-2-Phenyl-2-((R*)-1,4-dioxaspiro[4.5]decan-7-yl)-ethanol; and
rac-(R*)-2-Phenyl-2-((S*)-1,4-dioxaspiro[4.5]decan-7-yl)-ethanol.

48) Another embodiment relates to the compounds of formula 2 according to embodiment 42), selected from the group consisting of:
Methyl 2-phenyl-2-((R)-1,4-dioxaspiro[4.5]decan-7-yl)-acetate;
Methyl 2-phenyl-2-(1,4-dioxaspiro[4.5]decan-7-yl)-acetate;
rac-(R*)-Methyl 2-phenyl-2-((R*)-1,4-dioxaspiro[4.5]decan-7-yl)-acetate; and
rac-(R*)-Methyl 2-phenyl-2-((S*)-1,4-dioxaspiro[4.5]decan-7-yl)-acetate.

49) Another embodiment relates to the compounds of formula 6 according to embodiment 45), selected from the group consisting of:
(1R,2S,3S,4R)-6-oxo-3-phenylbicyclo[2.2.2]octan-2-yl methanesulfonate; and
rac-(1S*,2R*,3R*,4S*)-6-oxo-3-phenylbicyclo[2.2.2]octan-2-yl methanesulfonate.

50) A further aspect of the present invention relates to a process according to any one of embodiments 28) to 34), wherein the compound of the formula (I), wherein in this particular case Ar represents phenyl, is further transformed to any one of the following compounds:
rac-isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester,
isobutyric acid (1S,2S,4S)-2-(2-{[3-(4,7-dimethoxy-1H-benzoimidazol-2-yl)-propyl]-methyl-amino}ethyl)-5-phenyl-bicyclo[2.2.2]oct-5-en-2-yl ester; or especially
isobutyric acid (1R,2R,4R)-2-(2-{[3-(4,7-dimethoxy-1H-benzoimidazol-2-yl)-propyl]-methyl-amino}ethyl)-5-phenyl-bicyclo[2.2.2]oct-5-en-2-yl ester.

Such multistep transformation according to embodiment 50) is described especially in WO2009/130679 (examples 1A, 2A, 3A), which reference is incorporated in its entirety:

In a first step, the compound of formula (I), wherein in this particular case Ar represents phenyl (and wherein it is well understood that said compound of formula (I) may be used in racemic or the appropriate enantiomerically enriched form), is transformed to (1R*,2R*,4R*)-2-hydroxy-5-phenyl-bicyclo[2.2.2]oct-5-en-2-yl)-acetic acid tert.-butyl ester; which in turn is deprotected to the compound (1R*,2R*,4R*)-(2-hydroxy-5-phenyl-bicyclo[2.2.2]oct-5-en-2-yl)-acetic acid; which in turn is coupled with 3-(4,7-dimethoxy-1H-benzoimidazol-2-yl)-propyl]-methyl-amine to give (1R*,2R*,4R*)—N-[3-(4,7-dimethoxy-1H-benzoimidazol-2-yl)-propyl]-2-(2-hydroxy-5-phenyl-bicyclo[2.2.2]oct-5-en-2-yl)-N-methyl-acetamide; which in turn may be reduced to (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-ol; which in turn may be acylated to the compound (1R*,2R*,4R*)-2-(2-{[3-(4,7-dimethoxy-1H-benzoimida-zol-2-yl)-propyl]-methyl-amino}-ethyl)-5-phenyl-bicyclo[2.2.2]oct-5-en-2-yl ester, which is a calcium channel blocker.

The term "—$OR^1$ and —$OR^2$, together with the carbon atom to which they are attached to, represent a ketal group" encompasses any ketal group suitable to protect a ketone of formula 1c:

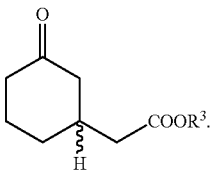

Formula 1c

The term especially encompasses ketal groups wherein $R^1$ and $R^2$ independently represent $C_{1-8}$-alkyl which is optionally substituted with aryl, $C_{1-6}$-alkoxy, hydroxy, or halogen; or $R^1$ and $R^2$ together form a group —$(CH_2)_n$—, wherein n represents the integer 2, 3, or 4, which group is optionally substituted with aryl, or $C_{1-4}$-alkyl. In a sub-embodiment, the term encompasses ketal groups wherein $R^1$ and $R^2$ independently represent $C_{1-8}$-alkyl (notably $C_{1-4}$-alkyl); or $R^1$ and $R^2$ together form a group —$(CH_2)_n$—, wherein n represents the integer 2 or 3, which group is optionally substituted with $C_{1-4}$-alkyl. In a further sub-embodiment, the term notably encompasses ketal groups wherein $R^1$ and $R^2$ together form a group —$(CH_2)_n$—, wherein n represents the integer 2 or 3 (notably 2).

The term "—$COOR^3$ represents an ester group" encompasses any ester group suitable to protect a carboxylic acid of formula 1d or of formula 1e:

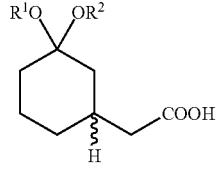

Structure 1d

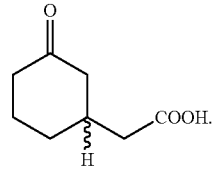

Structure 1e

The term especially encompasses ester groups wherein $R^3$ represents $C_{1-8}$-alkyl which is optionally substituted with aryl, $C_{1-6}$-alkoxy, hydroxy, or halogen. In a sub-embodiment, the term encompasses ester groups wherein $R^3$ represents $C_{1-8}$-alkyl or benzyl. In a further sub-embodiment, the term encompasses ester groups wherein $R^3$ represents $C_{1-3}$-alkyl, especially $R^3$ represents methyl.

Likewise, in the meaning of the term "—$COOR^{31}$ represents an ester group" $R^{31}$ represents $C_{1-8}$-alkyl which is optionally substituted with aryl, $C_{1-6}$-alkoxy, hydroxy, or halogen; in addition, $R^{31}$ is preferably identical to $R^3$. In a sub-embodiment, the term encompasses ester groups wherein $R^{31}$ represents $C_{1-8}$-alkyl or benzyl. In a further sub-embodiment, the term encompasses ester groups wherein $R^{31}$ represents $C_{1-3}$-alkyl, especially $R^{31}$ represents methyl. Any $R^{31}$ may be transformed into the corresponding $R^3$ using well known methods of trans-esterification.

It is well known that in transition metal-catalyzed alpha-arylations of carbonyl-containing compounds an ester group may in some instances be replaced by a cyano group. The inter-transformation of carboxylic acid/ester groups to cyano groups, or of cyano groups to carboxylic acid/ester groups is well known in the art. The use of such cyano groups is encompassed in the scope of the present invention.

The use of protecting groups for ketones and carboxylic acids is well known in the art (see for example "Protective Groups in Organic Synthesis", T. W. Greene, P. G. M. Wuts, Wiley-Interscience, 1999).

The term "any group which may be introduced by an organometallic reagent" as used for the substituent $R^4$ means all kinds of residues which may be installed via a organometallic reagent which is capable of making an addition reaction on a ketone carbonyl group. Especially, the term represents any residue which may be introduced using an organolithium, organomagnesium, organoboron, organoaluminium or organozinc reagent; notably organolithium, organomagnesium, or organoboron reagent. Examples of such residues are alkyl; aryl; alkenyl; and alkyl which is substituted with one or more substituents selected from fluoro, alkoxy, aryl, and —CO—$R^5$ wherein $R^5$ is alkyl or alkoxy. In addition, in some instances also heteroaryl groups such as especially 5- or 6-membered heteroaryl may be introduced via an organometallic reagent. Preferred examples of such residues are alkyl and aryl.

The term "aryl" as used herein means a phenyl or naphthyl group (preferably a phenyl group) which group is unsubstituted (preferred), or mono-, di-, or tri-substituted, wherein the substituents are independently selected from the group consisting of $(C_{1-4})$alkyl, $(C_{1-4})$alkoxy, halogen, $(C_{1-3})$fluoroalkyl, and $(C_{1-3})$fluoroalkoxy.

The term "heteroaryl" means a 5- to 10-membered monocyclic or fused bicyclic aromatic ring containing 1 to a maximum of 4 heteroatoms independently selected from oxygen, nitrogen and sulfur. Examples of monocyclic heteroaryl groups are 5-membered monocyclic heteroaryl groups such as furanyl, oxazolyl, isoxazolyl, oxadiazolyl, thienyl, thiazolyl, isothiazolyl, thiadiazolyl, pyrrolyl, imidazolyl, pyrazolyl, triazolyl, and tetrazolyl; and 6-membered monocyclic heteroaryl such as pyridyl, pyrimidyl, pyridazinyl, and pyrazinyl. Examples of bicyclic heteroaryl groups comprise 8-membered bicyclic heteroaryl groups such as 4H-furo[3,2-b]pyrrolyl, pyrrolo[2,1-b]thiazolyl and imidazo[2,1-b]thiazolyl; 9-membered bicyclic heteroaryl groups such as indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, pyrazolo[1,5-a]pyridyl, pyrazolo[1,5-a]pyrimidyl, imidazo[1,2-a]pyridyl, 1H-pyrrolo[3,2-b]pyridyl, and 1H-pyrrolo[2,3-b]pyridyl; and 10-membered bicyclic heteroaryl groups such as quinolinyl, isoquinolinyl, naphthyridinyl, cinnolinyl, quinazolinyl, quinoxalinyl, and phthalazinyl.

The term "alkyl", used alone or in combination, refers to a saturated straight or branched chain alkyl group containing one to eight carbon atoms. The term "$(C_{x-y})$alkyl" (x and y each being an integer), refers to an alkyl group as defined before containing x to y carbon atoms. For example a $(C_{1-4})$ alkyl group contains from one to four carbon atoms. Examples of alkyl groups are especially $(C_{1-4})$alkyl groups such as methyl, ethyl, propyl, isopropyl, n-butyl, isobutyl, sec.-butyl, and tert. butyl. Preferred are methyl and ethyl. Most preferred is methyl.

The term "alkenyl" as used herein, alone or in combination, refers to a straight or branched hydrocarbon chain containing two to six carbon atoms with at least one carbon-carbon double bond. The term "$(C_{x-y})$alkenyl" (x and y each being an integer), refers to an alkenyl group as defined before containing x to y carbon atoms. Representative examples of alkenyl include, but are not limited to, ethenyl (also referred to as "vinyl"), 2-propenyl (also referred to as "allyl"), 2-methyl-2-propenyl, 3-butenyl, 4-pentenyl, and 5-hexenyl, especially ethenyl or 2-propenyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are especially $(C_{1-4})$alkoxy groups such as methoxy, ethoxy, n-propoxy, isopropoxy, n-butoxy, isobutoxy, sec.-butoxy and tert.-butoxy. Preferred are ethoxy and especially methoxy.

The term "fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$ fluoroalkyl group contains from one to three carbon atoms in which one to seven hydrogen atoms have been replaced with fluorine. Representative examples of fluoroalkyl groups include trifluoromethyl and 2,2,2-trifluoroethyl. Preferred are $(C_1)$fluoroalkyl groups such as trifluoromethyl.

The term "fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy and 2,2,2-trifluoroethoxy. Preferred are $(C_1)$fluoroalkoxy groups such as trifluoromethoxy and difluoromethoxy.

The term "halogen" as used herein means fluoro, chloro, bromo or iodo, preferably chloro.

The term "solid-liquid separation" refers to routine solid-liquid separation techniques well known to a skilled person (see for example Perry's Chemical Engineers' Handbook, 7th edition, Perry, R. H.; Green, D. W. McGraw-Hill 1997). In particular, the term includes techniques such as filtration, centrifugation, and gravity sedimentation; especially filtration.

The term "liquid-liquid extraction" refers to routine liquid-liquid extraction or washing techniques well known to a skilled person (see for example Perry's Chemical Engineers' Handbook, $7^{th}$ edition, Perry, R. H.; Green, D. W. McGraw-Hill 1997). In particular the term includes washing or extraction techniques using settlers, cyclones, centrifuges, mixer-settler, all kinds of continuous contact equipment; distillation: batch and continuous distillation; and supercritical fluid separation techniques.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In case the term about is placed before a range, the respective interval is to be applied to both values of the range. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

Whenever the word "between" or "to" is used to describe a numerical range, it is to be understood that the end points of the indicated range are explicitly included in the range. For example: if a temperature range is described to be between 40° C. and 80° C. (or 40° C. to 80° C.), this means that the end points 40° C. and 80° C. are included in the range; or if a variable is defined as being an integer between 1 and 4 (or 1 to 4), this means that the variable is the integer 1, 2, 3, or 4.

The expression % w/w refers to a percentage by weight compared to the total weight of the composition considered. Likewise, the expression v/v refers to a ratio by volume of the two components considered. Likewise, the expression % a/a refers to the purity with respect to area under the curve (i.e. integral) in a chromatogram, preferably measuring the UV absorption. The expression "vol" signifies volumes (in L, e.g. of solvent) per weight (in kg, e.g. of reactant). For example 7 vol signifies 7 liters (of solvent) per kg (of reactant).

The term "enriched", for example when used in the context of enantiomers or diastereoisomers is understood in the context of the present invention to mean especially that the respective enantiomer/diastereoisomer is present in a ratio (mutatis mutandis:purity) as explicitly specified; usually in a ratio of at least 60:40, especially of at least 70:30, and notably of at least 90:10 (mutatis mutandis:purity of 60%/70%/90%) with respect to the respective other enantiomer/diastereoisomer(s). Preferably the term refers to the respective essentially pure enantiomer/diastereoisomer.

The term "essentially", for example when used in a term such as "essentially pure" is understood in the context of the present invention to mean especially that the respective stereoisomer/composition/compound etc. consists in an amount of at least 90, especially of at least 95, and notably of at least 99 percent by weight of the respective pure stereoisomer/composition/compound etc.

The relative configuration of stereoisomers is denoted as follows: for example, (1R*,4R*,5S*,6S*)-6-hydroxy-5-phenylbicyclo[2.2.2]octan-2-one, if not explicitly mentioned as racemate, denominates (1R,4R,5S,6S)-6-hydroxy-5-phenylbicyclo[2.2.2]octan-2-one, or (1S,4S,5R,6R)-6-hydroxy-5-phenylbicyclo[2.2.2]octan-2-one, or any mixture of these two enantiomers.

According to the invention, the compounds of Formulae (I) and (II) are manufactured by the methods given below. In general, they are prepared according to the general sequence of reactions outlined below in the General Reaction Schemes 1 to 11.

The starting materials, i.e. the compounds of formula 15 can be obtained using the procedures described in the literature (Shibasaki et al., *Tetrahedron* 2004, 60, 9569-9588). They can be obtained either in enantiomerically enriched form, or in form of the racemates.

In the following General Reaction Schemes the reaction sequence is illustrated for the variant using enantiomerically enriched starting materials of formula 15. However, this presentation shall be in no way be understood as limiting the present process to such enantioselective route. In the following, the substituents $R^1$ to $R^4$ and aryl have the particular meanings given in embodiment 1).

General Reaction Scheme 1:

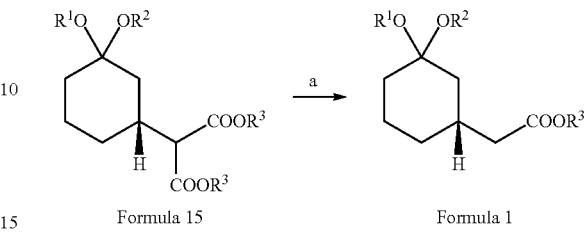

Formula 15            Formula 1

Preferably, in step a, the compound of formula 15 (here: the enantiomerically enriched form); wherein preferably $R^3$ represents methyl, and $R^1$ and $R^2$ together represent —$CH_2$—$CH_2$—; is treated with an alkali metal halide in an amount of 2-5 equ. and water in an amount of 1-2 equ. (both per equ. of the compound of formula 15) in a polar aprotic solvent such as DMSO, DMF, N-methylpyrrolidinone or dimethylacetamide, at elevated temperature. Preferred solvents are N-methylpyrrolidinone and dimethylacetamide, particularly dimethylacetamide. A preferred alkali metal halide is LiCl (preferably 2 equ.). Water is used in a preferred amount of 1 equ. A suitable reaction temperature is about 120-150° C., especially about 135-145° C., particularly about 140° C. The concentration of compound of formula 15 in the solvent is about 2-3 vol. (2-3 L solvent per kg; especially about 2.6 vol.). The reaction time is usually 2-5 h, especially 2-3 h. After completion of the reaction the mixture is filtered, the cake is washed with toluene (preferably about 0.5 vol.) and the filtrate is washed with water (preferably 3×2 vol.) to obtain the compounds of formula 1, usually as low viscous oil, in yields higher than about 88% and GC purity of about 97% a/a.

The technical advantage of this step is:
Compounds of formula 1 are obtained with no erosion of the enantiomeric purity.
The yield is substantially higher than in published protocols using compounds of formula 15 (66% yield with DABCO, see S. Blechert et al., *J. Am. Chem. Soc.* 2004, 126, 3534), whereas with the free ketone, corresponding to compounds of formula 14, the yield was 52% (using LiCl/DMSO, see J. Mattay et al., *Tetrahedron Asymmetry* 2006, 17, 993).
The process is very concentrated and leads to higher time-space yield.
The process is much faster and requires less unit operations than processes in published protocols using compounds of formula 15 (17 h reaction time in DMSO, followed by aqu. work-up in ethyl acetate and flash chromatography, see M. Shibasaki et al., *Tetrahedron* 2004, 60, 9569).
The process is simple as compared to alternative processes (84-90% yield with free ketone, corresponding to compounds of formula 14, via enzymatic hydrolysis followed by decarboxylation, usually in DMSO and/or water (S. Ley et al., *Chem. Eur. J.* 2008, 14, 6155).
The compound of formula 1 is obtained by a simple filtration of the reaction mixture, thus minimizing significantly the solvent volumes and reducing the number of unit operations. Normally, after completion of the reaction, the lithium salts are first dissolved by water, followed by a solvent exchange to a non water-miscible solvent.

General Reaction Scheme 2:

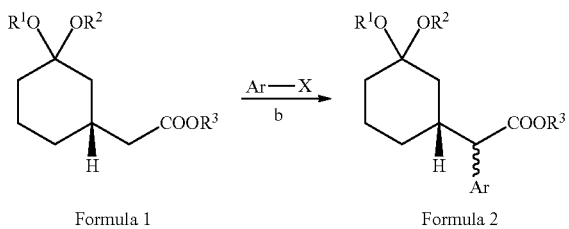

Formula 1                    Formula 2

In step b, compounds of formula 1 are alpha-arylated with a commercially available halo-aryl (X=Cl, or Br; especially chloro- or bromo-benzene), in the presence of a base (such as lithium diisopropylamide, lithium dicyclohexylamide, lithium hexamethyldisilazide, sodium hexamethyldisilazide, potassium hexamethyldisilazide, potassium tert-butoxide), a catalyst (such as tris(dibenzylideneacetone)dipalladium, bis (dibenzylideneacetone)-palladium, palladium(II)acetate), a ligand (sterically large phosphines such as tri-tert-butylphosphine or its tetrafluoroborate salt) in a suitable solvent. The preferred base is lithium diisopropylamide and the preferred solvent is a mixture of toluene and hexane, e.g. in a ratio of 1:2 v/v. As base, lithium diisopropylamide is preferably used in an amount of 1-3 equ. per equ. of the compound of formula 1, particularly in an amount of 1.2 equ. The preferred catalyst is tris(dibenzylideneacetone)dipalladium in combination with the ligand tri-tert-butylphosphine tetrafluoroborate, each in an amount of 0.001-0.1 equ. per equ. of the compound of formula 1, preferably 0.002-0.01 equ., particularly 0.01 equ. The reaction is performed at about −5 to 40° C., preferably at about 0 to 30° C. The reaction time is about 1-10 h, especially 1-5 h, and preferably about 2 h. After completion of the reaction citric acid soln. is added, followed by a phase split. The org. phase is washed twice with water and then treated with charcoal (preferably 1 wt.). The vol. of the org. phase is adjusted by removal of solvent under reduced pressure. Preferably a 50-60% w/w soln. is obtained. This soln. is directly used in the ensuing reduction step c.

The surprising observation as compared to prior art is the high reactivity of lithium diisopropylamide, whereas in the literature metal hexamethyldisilazides or lithium dicyclohexylamide have been stated to be superior to lithium diisopropylamide (see J. F. Hartwig et al., *J. Am. Chem. Soc.* 2002, 124, 12557).

The technical advantage of step b is:
Toluene is the solvent used for work up of step b and for the reaction of step c, thus reducing the number of solvents and unit operations.

General Reaction Scheme 3:

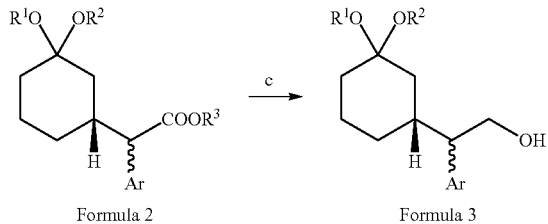

Formula 2                    Formula 3

In step c compounds of formula 2 are reduced, e.g. with LiAlH$_4$ in a solvent like toluene, THF, or 2-methyl THF, or mixtures thereof, to give compounds of formula 3. The preferred solvent is a mixture of toluene and THF in a ratio of 3.8:1. The concentration of the compound of formula 2 in the solvent is about 3-6 vol. (2-6 L solvent per equ.; especially about 3.7 vol.). LiAlH$_4$ is used in amounts of 0.5-2 equ. per equ. of the compound of formula 2, particularly in an amount of 0.55 equ. The reaction is carried out by adding a soln. of LiAlH$_4$ in THF into a soln. of the compound of formula 2 in toluene at about 5-15° C. The mixture is quenched after about 30-60 min by the consecutive addition of: 1.) a mixture of water (0.07 vol.) in THF (0.2 vol.), 2.) 30% NaOH (0.07 vol.) and 3.) water (0.22 vol.) at 10-20° C. After filtration over charcoal the solvent is removed to afford compounds of formula 3, usually as an oil, with high yield (>95%) in high purity (>95% a/a GC). In a preferred variant of this reaction toluene is stripped off under reduced pressure to reach a final content of toluene below 2% w/w in the compound of formula 3.

The technical advantage of step c is:
Toluene is the solvent used both for step b and c, thus minimizing volumes and number of unit operations.
The reaction and quench are highly concentrated.

General Reaction Scheme 4:

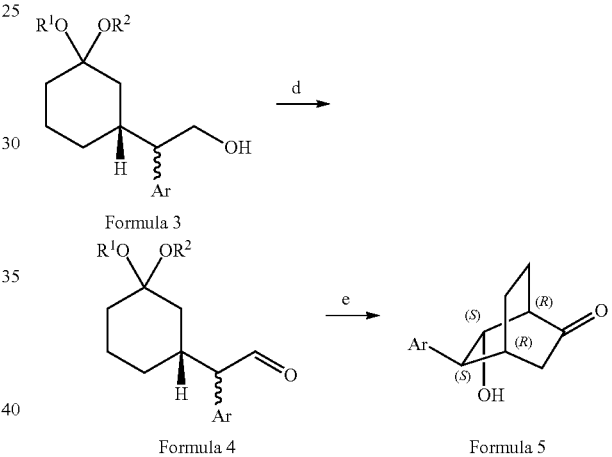

Formula 3

Formula 4                    Formula 5

In step d, compounds of formula 3 are reacted with commercially available bleach (12-14% w/w) in the presence of KBr and 2,2,6,6-tetramethylpiperidine-1-oxyl to obtain the compound of formula 4. Appropriate solvents are aromatic solvents (such as toluene or benzene), esters (such as EtOAc or iPrOAc) or chlorinated hydrocarbons (such as DCM). A preferred solvent is EtOAc. The amount of bleach (NaOCl soln.) is 1.0-1.5 equ. per equ. of the compound of formula 3, preferably 1.1-1.2 equ. The amount of both KBr and 2,2,6,6-tetramethylpiperidine-1-oxyl is 0.005-0.02 equ. per equ. of the compound of formula 3, preferably 0.01 equ. The reaction is carried out at about 0-20° C., preferably at about 5-10° C. After completion of the reaction the excess bleach is quenched by sodium thiosulfate soln., the org. phase washed with water and brine and evaporated to dryness to afford compounds of formula 4 as a mixture of diastereomers (60:40 to 70:30), usually as an oil. In a variant of step d, the org. layer containing the compound of formula 4 is filtered over Celite to remove traces of solid particles. In another variant of step d, the compound of formula 4 is not isolated: only a water and a brine wash are performed followed by adjustment of the concentration by distillation of EtOAc, and the reaction is continued with step e. In another variant of this reaction the residual toluene content in the starting material (i.e. the neat oil of 3) is reduced and controlled below 2% w/w by removal of solvent under reduced pressure.

The technical advantage of step d is:
The same solvent is used for steps d and e allowing for a telescoping of the organic layer containing the compound of formula 4 into step e.
This telescoping also minimizes additional unit operations which could impart thermal stress on compounds of formula 4.

In step e compounds of formula 4 are cyclized to afford compounds of formula 5 [corresponding to the enantiomerically enriched diastereoisomer of formula (IIa)]. Preferably the cyclization is run in the presence of an acid. Suitable solvents are aromatic solvents (such as toluene or benzene), esters (such as EtOAc or iPrOAc), alcohols (such as methanol, ethanol, isopropanol), ethers (such as THF, 2-methyltetrahydrofurane, 1,4-dioxane or tert-butylmethylether), ketones (such as acetone), chlorinated hydrocarbons (such as DCM), or acetonitrile. Preferred solvent is EtOAc. Suitable acids are aqu. mineral acids (such as aqu. HCl or HBr) or aqu. $H_3PO_4$. Preferred acid is aqu. HCl in a concentration of about 3-32%, preferably about 32%. The amount of the acid is about 0.1-2 equ. per equ. of the compound of formula 4, notably about 0.1-1 equ., especially about 0.3 equ. The reaction is carried out at about 20-75° C., notably at about 45-70° C., especially at about 50° C. The concentration of the compound of formula 4 in EtOAc is about 1-5 vol. (i.e. about 1-5 L EtOAc per kg of the compound of formula 4), especially about 1-2 vol. The reaction time is about 1-5 h, especially about 2-3 h. After completion of the reaction the mixture is worked up by solid-liquid separation. For example it is cooled to about 10° C., stirred at this temperature for about 16 h and filtered, followed by a wash of the filter cake with EtOAc to afford compounds of formula 5 in isomerically pure form (>99%) as a colorless crystalline solid. In a variant of step e, the suspension of the compound of formula 5 is cooled to about 0° C., and stirred at about 0° C. for about 1-5 h prior to filtration.

The technical advantage of step e is:
The same solvent is used for steps d and e allowing for a telescoping of the organic layer containing the compound of formula 4 into step e.
This telescoping minimizes additional unit operations which would impart thermal stress on compounds of formula 4.
The cyclization runs under milder conditions (such as lower temperature, milder acid, less equ. of acid, and shorter reaction time) as compared to prior art using the des-phenyl substrate (5M phosphoric acid/THF 1:1, reflux, 4 h, see J. Mattay et al., *Tetrahedron: Asymmetry* 2006, 993).
This cyclization affords the desired isomer of the compound of formula 5 with an easier work-up as compared to prior art using the des-phenyl substrate, thus reducing unit operations ((i) neutralization with NaOH, (ii) evaporation to dryness, (iii) aqu. work-up, extraction with DCM, (iv) water and brine wash of the DCM layer, (v) drying over $Na_2SO_4$, (vi) flash chromatography with petroleum ether and diethyl ether, see Bettolo et al., *Helv. Chim. Acta* 1998, 81, 2375; and similar work-up in J. Mattay et al., *Tetrahedron: Asymmetry* 2006, 993).
Furthermore, the process leads to the compounds of formula (II) in unpredictably high diastereoisomeric excess. The diastereomeric purity of the major isomer as formed in the reaction mixture is usually higher than 70%.

When isolated by solid-liquid separation, the compounds of formula (II) are obtained in high diastereoisomeric purity (mixture of compounds of formula (IIa) and (IIb) depending on the enantiomeric purity of the compounds of formula 1 used in step b; in general >99% diastereoisomeric purity.

When enantiomerically enriched epimers of the starting materials (resulting from enantiomerically enriched compounds of formula 1) are used, the enantiomeric excess is conserved during the cyclization step e.

The isolated yields are higher, between 60 and 70% as compared to the published protocols. Starting with compounds of Structure 4, where the phenyl substituent is not present, the yields are lower (38% yield after aqu. work-up and flash chromatography, see J. Mattay et al., *Tetrahedron: Asymmetry* 2006, 993; 61% yield after aqu. work-up and flash chromatography, see M. Bettolo et al., *Helv. Chim. Acta* 1998, 81, 2375).

General Reaction Scheme 5:

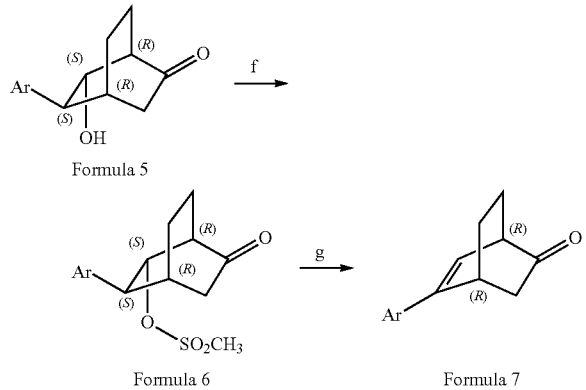

In step f, compounds of formula 5 [here: corresponding to the enantiomerically enriched diastereoisomer of formula (IIa)] are transformed into the corresponding mesylate derivatives of formula 6, in the presence of a base. Suitable solvents are aromatic solvents (such as toluene or benzene), ethers (such as THF, 2-methyltetrahydrofurane, 1,4-dioxane or tert-butylmethylether), polar aprotic solvents (such as DMSO, DMF, N-methylpyrrolidinone or dimethylacetamide) or chlorinated hydrocarbons (such as DCM). Most preferred solvent is toluene. The preferred reagent is methanesulfonyl chloride which is used in about 1-2 equ. per equ. of the compound of formula 5, preferably in about 1.3 equ. Appropriate bases are triethylamine, diethylisopropylamine or pyridine in amounts of about 1.5-3 equ. per equ. of the compound of formula 5, preferably in about 1.5 equ. The reaction is carried out at about 10-25° C. for about 10-60 min. After completion of the reaction water is added, followed by phase separation and a solvent exchange to the solvent of step g. Alternatively, the activation can be achieved by reacting the compound of formula 5 with benzoyl chloride in the presence of triethylamine in DCM at r.t. Alternatively, compounds of formula 6 can be obtained in crystalline form by crystallization from heptane/EtOAc (1:1 v/v) or toluene.

In step g, compounds of formula 6 are transformed into compounds of formula 7 by elimination of methanesulfonic acid. Suitable solvents are aromatic solvents (such as toluene, benzene, chlorobenzene, or xylenes), polar aprotic solvents (such as DMSO, sulfolane, DMF, N-methylpyrrolidinone or dimethylacetamide), higher boiling nitriles (such as acetonitrile or butyronitrile), higher boiling ethers (such as bis(2-methoxyethyl)ether), higher boiling nitrogen bases (such as 1,8-diazabicyclo[5.4.0]undec-7-en or 1,5-diazabicyclo(4.3.0)non-5-ene), or pyridines (such as pyridine, 2,6-lutidine or 2,4,6-collidine). The reaction is carried out at about 85-160° C., preferably at about 100-150° C. The reaction time is varying from 10 min-16 h, usually it is about 0.5-2 h.

In a preferred variant, the reaction step g is performed in the presence of bases using the solvents mentioned above. In this case, when basic solvents such as the above mentioned higher boiling nitrogen bases or pyridines are used, such solvents may serve at the same time as solvent and as base. Generally, suitable bases are amidine or guanidine bases (such as 1,8-diazabicyclo[5.4.0]undec-7-ene, 1,5-diazabicyclo(4.3.0)non-5-ene, 7-methyl-1,5,7-triazabicyclo[4.4.0]dec-5-ene), tertiary amines (such as 1,4-diazabicyclo[2.2.2]octane or tetramethylpropylene diamine), inorganic bases (such as potassium carbonate, lithium carbonate), or alcoholates (such as lithium-, sodium- or potassium salts of methanol, ethanol or tert-butyl alcohol). The bases are used in amounts of about 1-10 equ. per equ. of the compound of formula 6, preferably about 1-2 equ. When used as solvent and base at the same time, such bases are used in amounts of about 1-15 vol, notably 5-10 vol, with respect to the compound of formula 6. Potential additives are iodides (such as NaI) or lithium salts (such as LiBr), used in amounts of about 0.1-1 equ. per equ. of the compound of formula 6. In a particular variant, the elimination is accomplished in the presence of 2 equ. of 1,8-diazabicyclo[5.4.0]undec-7-ene in toluene at about 140° C. for about 1 h. In another particular variant, the elimination is accomplished in the presence of about 1.5 equ. of $Li_2CO_3$ in 1,8-diazabicyclo[5.4.0]undec-7-ene at about 100° C. for about 0.5 h.

In a second variant, the reaction step g is carried out without a base, in the presence of silicium dioxide in DMSO.

In a third variant, the reaction step g is carried out without a base by heating the compound of formula 6 in a suitable solvent like o-xylene, chlorobenzene, 3-dimethyl-3,4,5,6-tetrahydro-2(1H)-pyrimidinone, DMSO, sulfolane, DMF, N-methylpyrrolidinone, pyridine, 2,6-lutidine or 2,4,6-collidine at 140-150° C. for 1-2 h. Preferred solvents for this embodiment are sulfolane, N-methylpyrrolidinone and 2,4,6-collidine, most preferred solvent is 2,4,6-collidine. The concentration of the compound of formula 6 is about 0.5-10 vol. (i.e. 0.5-10 L of solvent per equ. of the compound of formula 6), preferably about 1 vol. After completion of the reaction 1N hydrochloric acid is added followed by a suitable solvent (such as iPrOAc, EtOAc, toluene or heptane). Preferred solvents are iPrOAc, EtOAc or heptane. The org. phase is washed with diluted aqu. HCl and dried by azeotropic distillation.

In a preferred variant of step g, the compound of formula 7 is isolated by crystallization from suitable solvents like heptane, tert-butylmethylether, mixtures of heptane and tert-butylmethylether. Preferred solvent for crystallization is heptane.

In a further variant, the steps f and g are telescoped: the compound of formula 6 is thus obtained by simple filtration of the reaction mixture and the filtrate is stirred at about 135° C. for about 1-2 h to obtain the compound of formula 7.

Technical advantages of steps f and g:
Step g is highly concentrated, thus enabling a high throughput.
Steps f and g, especially in case the preferred process is used, lead to crude compounds of formula (I) with high chemical purity, thus enabling a further upgrade in purity by crystallization, especially in case the compound of formula (I) is a low melting solid which may be difficult to crystallize in case the crude product has low purity.
The two steps f and g can be telescoped and run in one pot, thus raising the efficiency.

General Reaction Scheme 6:

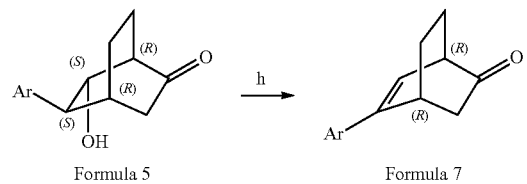

Formula 5                    Formula 7

Alternatively, compounds of formula 5 can be transformed into compounds of formula 7 without the intermediate formation of the compound of formula 6. In step h, the compounds of formula 5 are treated with suitable Bronsted or Lewis acids (such as acetic acid in combination or not with sodium acetate, polyphosphoric acid, thionyl chloride, phosphorylchloride, or diisopropylcarbodiimide in the presence of copper(I)chloride) in a solvent or neat, at about 50-150° C. for about 1-16 h. A preferred reagent is thionyl chloride. In this case, the reaction is carried out neat at about 50° C. for about 3 h.

General Reaction Scheme 7:

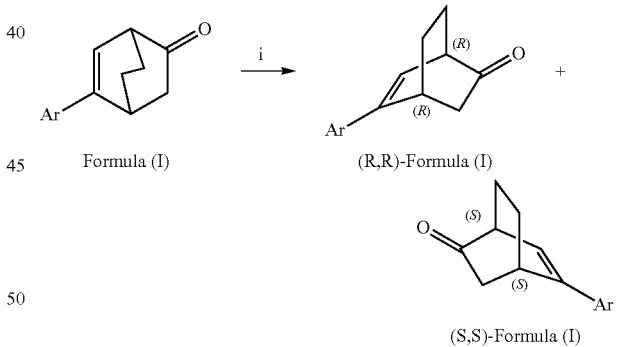

Formula (I)                (R,R)-Formula (I)

(S,S)-Formula (I)

Alternatively, in step i, racemic compounds of formula (I) can be separated in the two respective enantiomers: (R,R)-formula (I) and (S,S)-formula (I), by chromatography on chiral phase. Suitable solvents are mixtures of hydrocarbons and esters such as n-heptane and EtOAc, preferably 75:25 v/v; alternatively with 0.01-0.3% of triethylamine. In addition, methanol can be used as eluent (preferably with 0.01-0.3% of triethylamine). Suitable columns comprise Chiralpak AS-V or Chiralpak IA (e.g. 20 μm).

The technical advantage of step i is:
Both enantiomers are accessible, especially when used for the preparation of compounds of formula (III).
The separation on chiral stationary phase is highly efficient.

General Reaction Scheme 8:

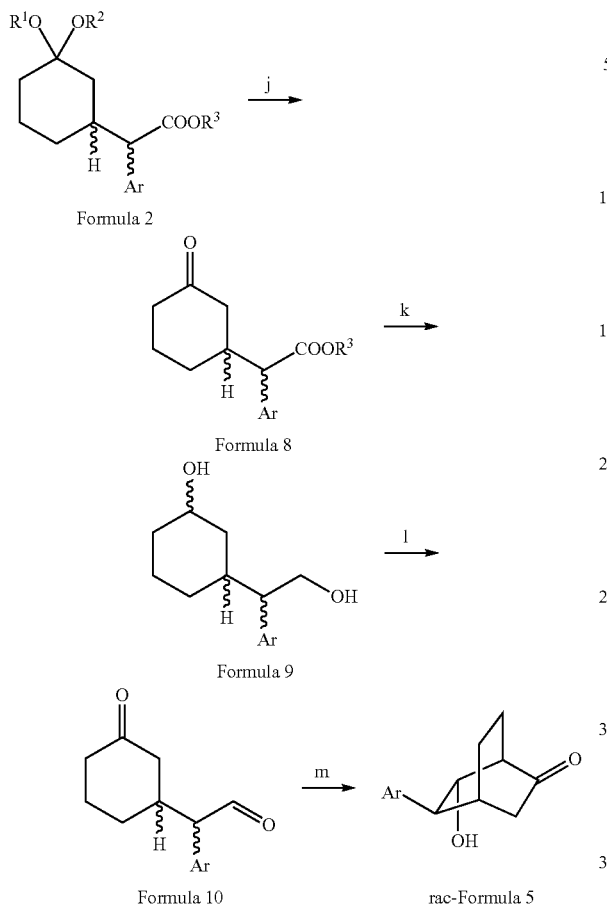

Formula 2

Formula 8

Formula 9

Formula 10    rac-Formula 5

Alternatively, compounds of formula 5 in racemic form [corresponding to the racemate of the preferred diastereoisomer of formula (II) as depicted in embodiment 4)] can be obtained by a sequence of reactions as depicted in General Reaction Scheme 8. In step j, compounds of formula 2 (isomeric mixture) are deprotected by reacting with an acid to obtain compounds of formula 8 (isomeric mixture). Appropriate solvents are ethers, esters, aromatic solvents, chlorinated solvents or alcohols, preferably THF. Suitable acids are mineral acids, preferably aqu. HCl.

In step k, both the ketone and the ester moiety of compounds of formula 8 (isomeric mixture) are reduced with lithium aluminium hydride in a solvent (like THF or 2-methyl THF, toluene and mixtures thereof) to obtain compounds of formula 9 (isomeric mixture).

In step l, both alcohol moieties of compounds of formula 9 (isomeric mixture) are oxidized with commercially available bleach (12-14% w/w) in the presence of KBr and 2,2,6,6-tetramethylpiperidine-1-oxyl to obtain compounds of formula 10 (isomeric mixture). Appropriate solvents are aromatic solvents (such as toluene or benzene), esters (such as EtOAc or iPrOAc) or chlorinated hydrocarbons (such as DCM). Preferred solvent is EtOAc.

In step m compounds of formula 10 (isomeric mixture) are cyclized in the presence of an acid to afford compounds of rac.-formula 5. Suitable solvents are aromatic solvents (such as toluene or benzene), esters (such as EtOAc or iPrOAc), alcohols (such as methanol, ethanol, isopropanol), ethers (such as THF, 2-methyltetrahydrofurane, 1,4-dioxane or tert-butylmethylether), ketones (such as acetone), chlorinated hydrocarbons (such as DCM), or acetonitrile. Preferred solvent is EtOAc. Suitable acids are aqu. mineral acids (such as aqu. HCl or HBr) or aqu. $H_3PO_4$. Preferred acid is aqu. HCl in a concentration of about 3-32%, preferably about 32%. The amount of the acid is about 0.1-2 equ. per equ. of compound of formula 10, notably about 0.1-1 equ., especially about 0.3 equ. The reaction is carried out at about 20-75° C., notably at about 45-70° C., especially at about 50° C. The reaction time is about 1-5 h, especially about 2-3 h. After aqu. work-up, the compounds of formula 5 are isolated in diastereomerically essentially pure form by crystallization from heptanes, tert-butylmethylether or mixtures thereof. The same processes may be used for enantiomerically enriched compounds depicted in General Reaction Scheme 8 to afford diastereomerically pure, enantioenriched compounds of formula 5.

General Reaction Scheme 9:

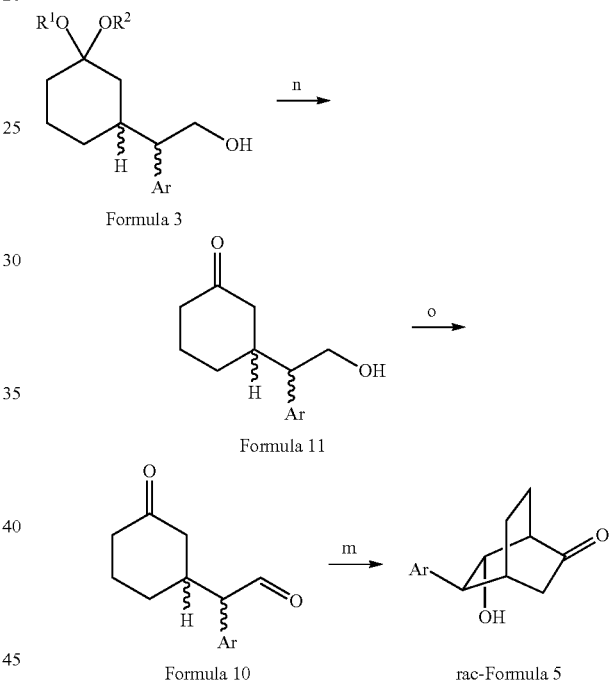

Formula 3

Formula 11

Formula 10    rac-Formula 5

Alternatively, compounds of formula 5 can be obtained by a sequence of reactions as depicted in General Reaction Scheme 9. In step n, compounds of formula 3 (isomeric mixture) are deprotected by reacting with an acid to obtain compounds of formula 11 (isomeric mixture). Appropriate solvents are ethers, esters, aromatic solvents, chlorinated solvents or alcohols, preferably THF. Suitable acids are mineral acids, preferably aqu. HCl.

In step o, the alcohol of compounds of formula 11 (isomeric mixture) is oxidized with commercially available bleach (12-14% w/w) in the presence of KBr and 2,2,6,6-tetramethylpiperidine-1-oxyl to obtain compounds of formula 10 (isomeric mixture). Appropriate solvents are aromatic solvents (such as toluene or benzene), esters (such as EtOAc or iPrOAc) or chlorinated hydrocarbons (such as DCM). Preferred solvents are DCM or EtOAc. Compounds of formula 5 are obtained in step m, as described in General Reaction Scheme 8. The same processes may be used for enantiomerically enriched compounds depicted in General Reaction Scheme 9 to afford diastereomerically pure, enantioenriched compounds of formula 5.

General Reaction Scheme 10:

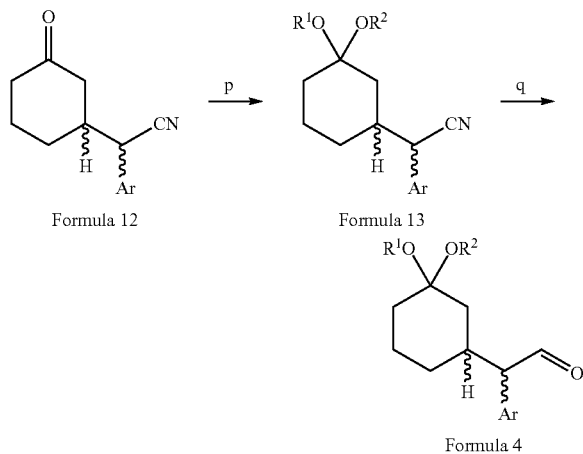

Alternatively, compounds of formula 4 can be obtained from the nitrile compounds of formula 12 which are known in literature in form of the racemates (T. Strzalko, J. Seyden-Penne, L. Wartski, J. Corset, M. Castella-Ventura, F. Froment, *J. Org. Chem.* 1998, 3295-3301). In step p, compounds of formula 12 (isomeric mixture) are protected as ketal using suitable alcohols, preferably ethylene glycol in the presence of an acid. Suitable solvents are ethers, aromatic solvents, chlorinated solvents or alcohols, preferably toluene. Suitable acids are aqu. mineral acids or sulfonic acids, preferably p-toluenesulfonic acid.

In step q, the nitrile group of the compounds of formula 13 (isomeric mixture) is reduced to the aldehyde of formula 4. A suitable reducing agent is diisobutylaluminum hydride. Suitable solvents are hydrocarbons, ethers, aromatic solvents and mixtures thereof, preferably a mixture of heptane and THF. The reaction temperature is between −80° C. and 30° C., preferably between 20° C. and 30° C. The same processes may be used for enantiomerically enriched compounds depicted in General Reaction Scheme 10 to afford diastereomerically pure, enantioenriched compounds of formula 5.

General Reaction Scheme 11:

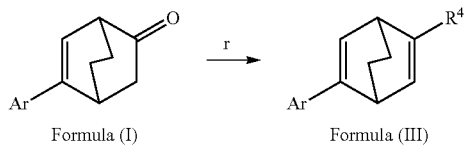

In step r, compounds of formula (I) may be transformed into compounds of formula (III). This can either be accomplished similar to published procedures (whereas the diketones are the substrates, using first the synthesis of the enol triflate which is then coupled with Grignard reagents in the presence of a Pd catalyst, see Hayashi et al., *J. Am. Chem. Soc.* 2004, 126, 13584) or by the successive treatment of (first substep) an organometallic reagent, followed by (second substep) dehydration. Suitable organometallic reagents are organolithium, organomagnesium, or organoboron compounds, preferably organomagnesium reagents (Grignard reagents). Additional metal salts can be added like cerium trichloride or lanthanum trichloride, zinc dichloride, copper chloride, lithium chloride, (trimethylsilyl)magnesium chloride, magnesium chlorid. The reaction with the organometallic reagent is performed between −80° C. and 30° C., preferably between −10 and 30° C. Suitable solvents for the first substep are ethers (like THF or 2-methyl THF, dimethoxymethane) and aromatic solvents (like toluene), preferably THF or toluene and mixtures thereof. In the second substep the intermediate is either treated with an acid, preferably aqu. mineral acids, most preferably aqu. HCl; or with a sulfonylchloride, especially methanesulfonylchloride. The second substep is carried out at 20-100° C., preferably at 20-40° C. Aqu. work-up affords the dienes which can be further purified by either chromatography or crystallization. In a variant, the compound of formula (I) may be added to the organometallic reagent. The processes depicted in General Reaction Scheme may similarly be used for enantiomerically enriched compounds to afford enantioenriched compounds of formula (III).

The technical advantages of step r is:
Both enantiomers of compounds of formula (III) can be synthesized by choosing the correct catalyst in the Shibasaki procedure to produce compounds of formula 14.
The synthesis is high yielding, efficient and amenable to large scale.
Flexibility exists in the synthesis of either $C_1$-or $C_2$-symmetrical chiral dienes with so far unprecedented effects on catalysis.
The following examples further illustrate the invention.

EXAMPLES

All temperatures given are external temperatures and are stated in ° C. Compounds are characterized by $^1$H-NMR (400 MHz) or $^{13}$C-NMR (100 MHz) (Bruker; chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz); internal standard for quantitative NMR was 1,4-dimethoxybenzene; by LC-MS, GC, and chiral HPLC (methods defined below); $t_R$ is given in minutes. Melting point is measured on Büchi melting point apparatus B540 and is not corrected. Unless stated otherwise, yields are given as is. Corrected yields are corrected with the NMR assay with internal standard of the starting material and the product.
GC-MS:
Thermo Trace GC Ultra, Thermo DSQ II MS detector, Thermo TriPlus Autosampler
Injection volume: 1 μL
Column: Zebron ZB-5-MS, 15 m×0.25 mm ID, 0.25 μm film
Column flow: 2 ml/min
Carrier gas: Helium
Split ratio: 20
SSL inlet temp.: 200° C.
Temp. gradient: 60-300° C. from 0 to 4.0 min, 300° C. isotherm from 4.0 to 5.0 min
Ionization: Chemical ionization with $CH_4$ as reagent gas
LC-MS Method 1:
Agilent G1956B (MS, Ionisation: BSI+, APCI), Agilent G1312B Bin Pump, Agilent G1315C DAD, Agilent G1316B (thermostated column compartment), Agilent G1367C (auto sampler)

Injection volume: 2 μL
Column: Kinetex C18, 2.6 μm, 2.1×50 mm
Column flow: 1 ml/min
Eluent: Eluent A: Water, 0.08% TFA (trifluoroacetic acid)
   Eluent B: Acetonitrile, 0.012% TFA Gradient:

| | |
|---|---|
| 2.0 min | 95% B |
| 2.8 min | 95% B |
| 3.0 min | 5% B |

Pressure: 380 bar
Temperature: 40° C.
Detection wavelength: 210 nm
LC-MS Method 2:
Same hardware as LC-method 1
Injection volume: 2 μL
Column: Eclipse Plus C18, 1.8 μm, 2.1×50 mm
Column flow: 1 ml/min
Eluent: Eluent A: Water, 0.08% TFA (trifluoroacetic acid)
   Eluent B: Acetonitrile, 0.012% TFA Gradient:

| | |
|---|---|
| 2.0 min | 95% B |
| 2.8 min | 95% B |
| 3.0 min | 5% B |

Pressure: 480 bar

Temperature: 50° C.

Detection wavelength: 210 nm

Chiral HPLC Method:

Dionex HPG-3400SD Bin pump, Dionex DAD-3000

Injection volume: 2 μL
Column: ChiralPak AS-H, 4.6×250 mm, 5 m
Column flow: 0.8 ml/min
Eluent: Heptane (60%)/2-propanol (40%)
Concentration: 4 mg/mL heptane/2-propanol 1:1
Detection: 210 nm
Temperature: 25° C.
Abbreviations (as Used Herein and in the Description Above):
aqu. aqueous
DCM Dichloromethane
DMAc Dimethylacetamide
DMF Dimethylformamide
DMSO Dimethylsulfoxide
DSC Differential Scanning Calometry
equ. equivalent(s)
EtOAc Ethyl acetate
h hour(s)
iPrOAc isopropyl acetate
IPC In Process Control
LC-MS Liquid Chromatography—Mass Spectrometry
GC-MS Gas Chromatography—Mass Spectroscopy
min. minute(s)
m.p. melting point
Ms Methanesulfonyl (mesyl, —$SO_2$—$CH_3$)
org. organic
rac. rac.
r.t. room temperature
soln. solution
TBME tert-butyl methyl ether
temp. temperature
THF Tetrahydrofurane
TLC Thin Layer Chromatography
$t_R$ retention time
% w/w Mass % (NMR assay)
% a/a Area % (purity by area %)

Example 1

Preparation of Compound 7 Using Method A

Scheme 1: Reaction sequence of steps a-g: Method A

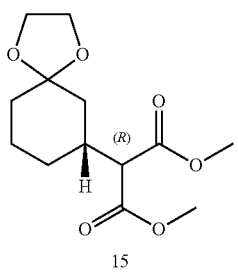

15

↓a

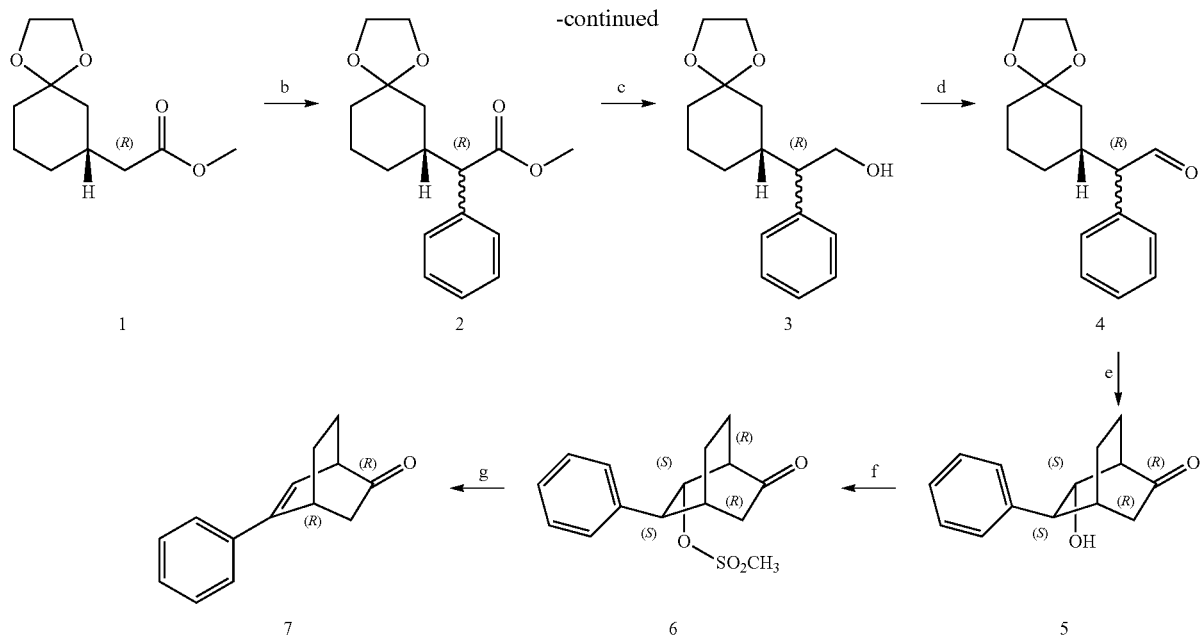

Compound 15 was synthesized according to published procedures, see for example M. Shibasaki et al.: *Angew. Chem. Int. Ed.* 1996, 35, 104-106, *Tetrahedron* 2004, 60, 9569-9588.

Compound 1

Methyl 2-((R)-1,4-dioxaspiro[4.5]decan-7-yl)-acetate

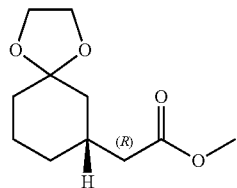

A 30 L steel-enameled reactor was charged with compound 15 ((R)-dimethyl 2-(1,4-dioxaspiro[4.5]decan-7-yl)malonate, 5.99 kg, 85% w/w) in DMAc (15 L). Water (0.4 L), LiCl (1.872 kg) were added. The soln. was heated at 120-136° C. over 5 h. After 120° C. was reached a precipitate formed and gas evolution started without foaming. IPC showed more than 99% conversion. The mixture was cooled to 30° C. and filtered over a 10 L nutsche filled with Celite (1.2 kg) and rinsed with toluene (3.5 L). The filtrate was charged into the reactor and washed three times with water (3×12 L). The org. phase was concentrated to dryness at 100° C. jacket temperature and 500-110 mbar to afford compound 1 as a low viscous oil. Yield: 4.2 kg (89%), NMR assay: 84% w/w (thereof 12% w/w toluene); GC-MS: 97% a/a, $t_R$=2.37, $[M+1]^+$=215; $^1$H-NMR (CDCl$_3$): δ=3.95 (s, 4H), 3.68 (s, 3H), 2.26 (d, J=6.9 Hz, 2H), 2.03-2.20 (m, 1H), 1.70-1.87 (m, 4H), 1.38-1.66 (m, 2H), 1.26 (t, J=12.5 Hz, 1H), 0.86-1.06 (m, 1H).

Compound 2

Methyl 2-phenyl-2-((R)-1,4-dioxaspiro[4.5]decan-7-yl)-acetate (mixture of diastereoisomers)

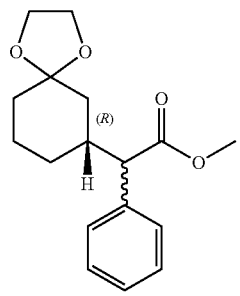

To a dry 30 L steel-enameled reactor was added 33% hexyl lithium in hexane (8.3 L) followed by toluene (16 L). Diisopropylamine (3.2 L) was added at 0-10° C. with cooling over 30 min followed by a toluene (0.5 L) rinse. (R)-methyl 2-(1, 4-dioxaspiro4.5decan-7-yl)acetate (compound 1, 4.0 kg, 86% w/w) was added neat at 5-10° C. with cooling over 45 min, followed by a toluene (1.5 L) rinse. The milky light-yellow mixture was stirred for 10 min at 5-10° C. Pd2(dba)$_3$ (172 g) and P(tBu)3.HBF4 (55 g) were added followed by inertization. Bromobenzene (2.94 kg) was degassed in the feed tank via 3 cycles of vacuum until bubbling occurred, followed by nitrogen purges. The bromobenzene was added at 10-15° C. over 15 min. The black mixture was warmed up to 20° C. by adjusting the jacket to 20° C. and was stirred for 2 h 45 min. An IPC (GC) showed 99% conversion. A solution of citric acid monohydrate (2.4 kg) in water (9.6 L) was added at 20-30° C. and the dark layers were separated. The org. phase is washed twice with water (2×12 L). Charcoal (400 g) was added to the org. phase and it was stirred at 20-30° C. for 30 min. Then the org. phase was filtered over a pad of Celite (750 g) followed by a final rinse of the filter cake with toluene (2 L). The org. phase was concentrated in the reactor at 60° C. jacket temperature and 210-58 mbar and finally adjusted to the desired concentration by the addition of toluene (0.4 vol., 1.6 L). This soln. (8.85 kg) was used in the next step. An aliquot was withdrawn, evaporated to dryness for yield and purity determination: 4.97 kg content of compound 2 as a red-brown oil. Yield: 5 kg (exact yield was determined after next step). NMR assay of aliquot: 82% w/w; GC-MS: 96% a/a, $t_R$=3.34, 3.38 (pair of isomers, 1:2), $[M+1]^+$=291.

Analytical reference samples of rac. compound 2 isomer 1 and isomer 2 were obtained by chromatography on silica gel with toluene/EtOAc (95:5) as eluent. The more polar isomer 1 (TLC) was further crystallized from TBME.

rac. Compound 2 Isomer 1

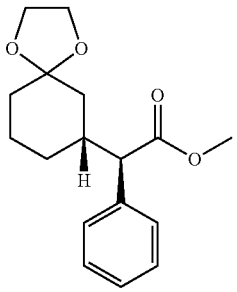

rac. Compound 2 Isomer 2

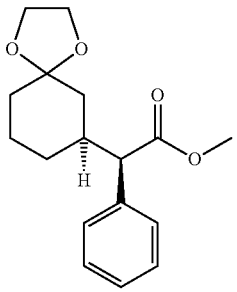

Reference Samples: Isomers of rac.-Compound 2

Rac. compound 2 Isomer 1, colorless crystalline solid, like configuration as proven by single crystal X-ray structure analysis; m.p.=87° C. (peak by DSC); TLC: $R_f$=0.30 (toluene/EtOAc 9:1); GC-MS: 97% a/a, $t_R$=3.43, $[M+1]^+$=291. LC-MS method 1: 100% a/a, $t_R$=1.74, $[M+1]^+$=291; $^1$H-NMR (CDCl$_3$): δ=7.23-7.41 (m, 5H), 3.93-4.08 (m, 4H), 3.66 (s, 3H), 3.30 (d, J=10.5 Hz, 1H), 2.33-2.46 (m, 1H), 1.84-1.93 (m, 1H), 1.61-1.80 (m, 2H), 1.26-1.56 (m, 4H), 0.70-0.85 (m, 1H); $^{13}$C-NMR (CDCl$_3$): δ=173.72, 137.58, 128.55, 128.51, 127.34, 108.92, 64.34, 64.27, 58.14, 51.80, 40.03, 38.98, 34.84, 29.02, 22.69.

Rac. compound 2 Isomer 2, yellow oil, unlike configuration by deduction with single crystal X-ray structure analysis of rac. compound 2 Isomer 1; TLC: $R_f$=0.33 (toluene/EtOAc 9:1); GC-MS: 96% a/a, $t_R$=3.41, $[M+1]^+$=291; LC-MS method 1: 95% a/a, $t_R$=1.67, $[M+1]^+$=291. $^1$H-NMR (CDCl$_3$): δ=7.23-7.39 (m, 5H), 3.72-3.95 (m, 4H), 3.66 (s, 3H), 3.31 (d, J=10.5 Hz, 1H), 2.34-2.48 (m, 1H), 1.33-1.86 (m, 6H), 0.97-1.15 (m, 2H); $^{13}$C-NMR (CDCl$_3$): δ=128.60, 127.34, 64.05, 64.1.5, 58.19, 51.81, 38.79, 38.60, 34.75, 30.50, 22.80.

Compound 3

2-Phenyl-2-((R)-1,4-dioxaspiro[4.5]decan-7-yl)ethanol (mixture of diastereoisomers)

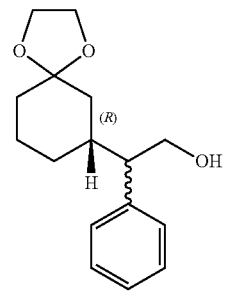

The reactor was charged with toluene (5.9 L) and a soln. of 2.4N LiAlH$_4$ in THF (3.9 L). The feed tank was charged with the toluene soln. (8.85 kg) of compound 2 (4.914 kg, 82% w/w of the residue) and additional toluene (3.9 L). This soln. was added to the LiAlH$_4$ soln. at 5-15° C. over 1 h. The reaction was stirred at 10-20° C. for 30 min. IPC (GC) indicated >99% conversion. A mixture of water (350 mL) and THF (990 mL) was added at 13-22° C. over 40 min. 15% NaOH-soln. (350 mL) was added at 10-20° C. over 20 min. Water (1.1 L) was added at 10-20° C. over 5 min. Charcoal (0.5 kg, granulated) was added and the mixture was stirred at 20° C. for 2 h prior to filtration over Celite (0.6 kg). The filter cake was washed with toluene (2 L). The filtrate was concentrated to dryness at 50-55° C. batch temperature and 500-25 mbar to afford compound 3 as a low viscous dark oil. Yield: 4.4 kg, 99%. Assay-corrected yield over two steps: 4 kg compound 1 (assay 86% w/w) gave 4.4 kg compound 3 (assay 81% w/w), 84% yield. NMR assay: 81% w/w (11% w/w toluene); GC-MS: 96% a/a, $t_R$=3.40, 3.49 (pair of isomers), $[M-18+1]^+$=245.

Analytical reference samples of rac. compound 3 isomer 1 and isomer 2 were obtained by chromatography on silica gel with heptane/EtOAc (8:2) as eluent. The more polar isomer 1 (TLC) was labelled isomer 1. The relative configuration is only tentatively assigned.

rac. Compound 3 Isomer 1

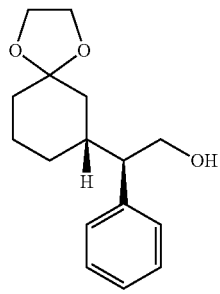

rac. Compound 3 Isomer 2

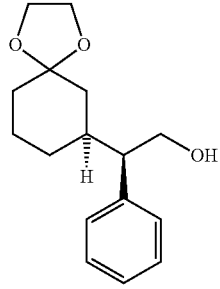

Reference Samples: Isomers of rac.-Compound 3

Rac. compound 3 Isomer 1, colorless oil; TLC: $R_f$=0.23 (toluene/EtOAc 7:3); GC-MS: 98% a/a, $t_R$=3.44, [M−18+1]$^+$= 245; LC-MS method 1: 98% a/a, [M−61]$^+$=201; $^1$H-NMR (CDCl$_3$): δ=7.16-7.44 (m, 5H), 3.77-4.05 (m, 6H), 2.58-2.73 (m, 1H), 1.88-2.11 (m, 2H), 1.16-1.85 (m, 7H), 0.63-1.03 (m, 1H); $^{13}$C-NMR (CDCl$_3$): δ=141.12, 128.77, 128.61, 126.84, 109.29, 64.74, 64.36, 64.23, 54.31, 40.13, 37.60, 34.74, 29.56, 22.93.

Rac. compound 3 Isomer 2, colorless oil; TLC: $R_f$=0.32 (toluene/EtOAc 7:3); GC-MS: 99% a/a, $t_R$=3.41, [M−18+1]$^+$= 245; LC-MS method 1: 100% a/a, $t_R$=1.36, [M−61]$^+$= 201; $^1$H-NMR (CDCl$_3$): δ=7.14-7.41 (m, 5H), 3.72-4.04 (m, 6H), 2.59-2.77 (m, 1H), 0.91-2.12 (m, 10H); $^{13}$C-NMR (CDCl$_3$): δ=140.88, 128.77, 128.66, 126.83, 109.18, 64.84, 64.18, 64.05, 54.25, 39.31, 37.40, 34.72, 30.03, 23.14.

Compound 4

2-Phenyl-2-((R)-1,4-dioxaspiro[4.5]decan-7-yl)acetaldehyde

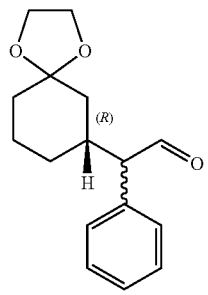

A bleach soln. with pH 8.5-9.5 was prepared: Commercial bleach was titrated with the KI/sodium bisulfite couple to determine its hypochlorite content: 1.9N, 12% w/w. This bleach soln. (65 mL) was diluted with aqu. sat. NaHCO$_3$-soln. (26.4 mL) to achieve pH 8.7

Compound 3 (28.9 g, 89% w/w) was dissolved in EtOAc (110 mL). A soln. of KBr (0.993 g) in water (2.2 mL) was added at 0° C., followed by 2,2,6,6-tetramethylpiperidine-1-oxyl (130 mg). The freshly prepared bleach soln. was added at 0-10° C. over 20 min with cooling. IPC (GC and LC-MS method 1) showed >98% conversion. Aqu. sat. sodium thiosulfate soln. (0.3 mL) was added at 10-15° C. until the test against KI (0.5N soln.)/starch (1% aqu. soln.) was negative. Water (65 mL) was added and the mixture filtered over Celite (30 g). The org. phase was extracted with ½-sat. NaCl-soln. (2×60 mL). Total mass of the EtOAc soln. was 124 g. An aliquot was withdrawn and evaporated to dryness for purity and yield determination: Yield: 27.4 g, 85% corr. for NMR assay.

Analytical data for aliquot: NMR assay: 79% w/w; GC-MS: 96% a/a, $t_R$=3.26, 3.30 (pair of isomers), [M+1]$^+$=261. $^1$H-NMR (CDCl$_3$,): δ=9.71 (d, J=3.2 Hz, 0.6H), 9.70 (d, J=3.3 Hz, 0.4H), 7.29-7.42 (m, 3H), 7.18-7.24 (m, 2H), 3.77-4.04 (m, 4H), 3.30-3.36 (m, 1H), 2.42-2.57 (m, 1H), 1.23-0.90 (m, 8H).

Compound 5

(1R,4R,5S,6S)-6-hydroxy-5-phenylbicyclo[2.2.2]octan-2-one

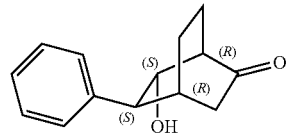

Steps d and e Telescoped:

A bleach soln. with pH 8.5-9.5 was prepared: Commercial bleach was titrated with the KI/sodium bisulfite couple to determine its hypochlorite content: 1.92N, 12% w/w. This bleach soln. (7.2 L) was diluted with aqu. sat. sodium bicarbonate-soln. (2.9 L) to achieve pH 9.3.

Compound 3 (3 kg, 81% w/w) was dissolved in EtOAc (15 L). A soln. of KBr (136.1 g) in water (300 mL) was added at 20° C., followed by 2,2,6,6-tetramethylpiperidine-1-oxyl (17.9 g). The freshly prepared bleach soln. was added at 4-8° C. over 45 min with cooling. IPC (GC and LC-MS method 1) showed >98% conversion. Aqu. sat. sodium thiosulfate soln. (50 mL) was added at 10-15° C. until the test against KI (0.5N soln.)/starch (1% aqu. soln.) was negative. The org. phase was washed with water (9 L) and ½-sat. NaCl-soln. (2×4 L). Solvent (9 L) was removed by distillation at 50° C. jacket at 250-150 mbar. The target concentration (2 vol. with respect to compound 3) was adjusted by the addition of EtOAc (2 L) to get a total vol. of 9 L. An aliquot was withdrawn and evaporated to dryness for purity and yield determination. Estimated mass was 3.095 kg compound 4 with NMR assay of 61% w/w (14% w/w EtOAc) corresponding to 1.86 kg compound 4, 78% corr. for NMR assay.

32% HCl (333 mL) was added at 25° C. and the mixture was stirred at 50° C. for 2 h. IPC (LC-MS method 1) showed >97% conversion. The mixture was cooled to 10° C., stirred at this temp. for 16 h, then further cooled to 0° C. and stirred at this temp. for 1 h. The suspension was filtered and washed with EtOAc (2×1.5 L). The filter cake was dried by applying vacuum for 2 h to afford compound 5 as colorless crystalline solid. Yield over two stages: 0.921 kg, 46% corr. for NMR assay.

M.p.=191° C.; NMR assay: 98% w/w; chiral HPLC method: enantiomeric ratio=100:0, diastereomeric purity: 100%; LC-MS method 1: 100% a/a, $t_R$=1.23, [M−18+1]$^+$= 199; $^1$H-NMR (CDCl$_3$): δ=7.34-7.42 (m, 4H), 7.27-7.32 (m, 1H), 4.48 (t, J=3.7 Hz, 1H), 2.93-2.97 (m, 1H), 2.58 (q, J=3.1 Hz, 1H), 2.49-2.56 (m, 1H), 2.35-2.44 (m, 2H), 1.87-1.95 (m, 3H), 1.72-1.83 (m, 1H), 1.42-1.53 (m, 1H); $^{13}$C-NMR (CDCl$_3$): δ=215.40, 142.21, 128.60, 127.56, 126.59, 74.37, 52.83, 51.50, 45.55, 34.42, 20.21, 18.22.

Compound 6

(1R,2S,3S,4R)-6-oxo-3-phenylbicyclo[2.2.2]octan-2-yl methanesulfonate

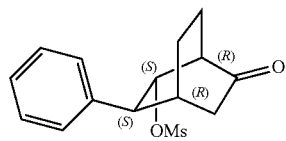

Compound 5 (25 g) was dissolved in DCM (125 mL) followed by triethylamine (24 mL). The suspension was cooled to 0° C. and methane sulfonyl chloride (11.6 mL) was added at 10-20° C. After 1.5 h, the mixture was washed filtered and the filtrate washed with water (3×125 mL). The org. phase was dried over Na$_2$SO$_4$ and concentrated to dryness under reduced pressure to afford compound 6 as a yellow oil, which solidified at r.t. Yield: 32.5 g, 96%.

20 g thereof were dissolved in heptane (350 mL) and EtOAc (350 ml) at 50° C. and filtered over silica gel (15 g). The filtrate was cooled to 0° C., filtered, and the filter cake was washed with heptane (100 mL) to afford a first crop of 22a as a colorless solid. Yield first crop: 8.33 g (42% recovery). Additional crystals were filtered off from the mother liquor to afford a second crop of 22a as a colorless solid. Yield second crop: of 2.75 g.

M.p.=87° C. (peak by DSC); LC-MS method 1: 100% a/a, t$_R$=1.4, [M−96+1]+=199; $^1$H-NMR (CDCl$_3$): δ=7.38-7.49 (m, 2H), 7.30-7.38 (m, 3H), 5.45 (t, J=3.8 Hz, 1H), 3.22-3.30 (m, 1H), 2.88-3.00 (m, 4H), 2.54-2.63 (m, 1H), 2.44-2.53 (m, 1H), 2.35-2.42 (m, 1H), 1.96-2.08 (m, 2H), 1.71-1.88 (m, 1H), 1.43-1.60 (m, 1H); $^{13}$C-NMR (CDCl$_3$): δ=210.97, 139.91, 129.03, 127.34, 82.51, 50.59, 48.58, 45.54, 39.45, 35.41, 20.21, 18.02.

Compound 7

(1R,4R)-5-phenylbicyclo[2.2.2]oct-5-en-2-one

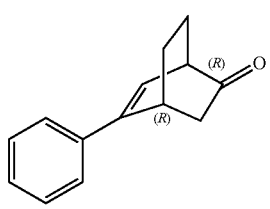

Steps f and g Together:

Toluene (6 L) was added to compound 5 (1.2 kg) followed by triethylamine (1.15 L). The suspension was cooled to 10° C. and methane sulfonyl chloride (0.56 L) was added at 10-20° C. IPC (LC-MS method 1) showed >99% conversion after 10 min. The mixture was washed with water (2×3 L) and concentrated to dryness under reduced pressure to afford compound 6 as a yellow oil, which solidified at r.t. Yield compound 6: 1.6 kg, 99%

NMR assay: 95% w/w. LC-MS method 1: 98% a/a, t$_R$=1.44, [M−96+1]+=199. $^1$H-NMR data in CDCl$_3$ correspond to the structure.

Compound 6 (1.6 kg) was dissolved in 2,4,6-collidine (1.2 L) and stirred at 140-145° C. for 1 h. IPC (LC-MS method 1) showed >99% conversion. 1N HCl (3 L) and heptane (19 L) were added and the layers separated. The org. phase was washed with 1N HCl (3 L), then with water (2×3 L) and filtered over Na$_2$SO$_4$ (1.7 kg). The cake was washed with heptane (3 L). Solvent (11.5 L) was removed from the filtrate at 110° C. jacket temp. under reduced pressure. At 40° C. seed crystals (compound 7, 300 mg) were added, the mixture stirred at 39-40° C. for 1 h, cooled to 0° C. within 0.5 h and stirred at 0° C. for 10 min. The suspension was filtered and the nutsche cake washed with heptane (1 L) to afford compound 7 as a beige crystalline solid. Yield first crop: 0.69 kg, 63%

M.p.=66.3-67.5° C.; NMR assay: 100% w/w; [α]$_D^{26}$+547° (CDCl$_3$) (compare with literature data: [α]$_D^{19}$+447° (CDCl$_3$), see: Kinoshita, T; Haga, K; Ikai, K; Takeuchi, K. Tetrahedron Lett. 1990, 31, 4057-4060); chiral HPLC method: enantiomeric ratio=100:0, diastereomeric purity: 100%; LC-MS method 1: 100% a/a, t$_R$=1.60, [M+1]+=199. $^1$H-NMR (CDCl$_3$): δ=7.44-7.49 (m, 2H), 7.36-7.43 (m, 2H), 7.29-7.36 (m, 1H), 6.46 (dd, J$_1$=6.7 Hz, J$_2$=2.2 Hz, 1H), 3.53-3.58 (m, 1H), 3.30-3.35 (m, 1H), 2.19-2.23 (m, 2H), 1.97-2.06 (m, 1H), 1.83-1.96 (m, 1H), 1.64-1.80 (m, 2H); $^1$H-NMR (CD$_3$OD): 7.48-7.55 (m, 2H), 7.34-7.43 (m, 2H), 7.22-7.33 (m, 1H), 6.49 (d, J=6.4 Hz, 1H), 3.55-3.62 (m, 1H), 3.22-3.30 (m, 1H), 2.09-2.30 (m, 2H), 1.88-2.04 (m, 2H), 1.59-1.83 (m, 2H). $^{13}$C-NMR (CDCl$_3$): δ=212.44, 147.95, 137.64, 128.69, 127.78, 124.85, 122.10, 49.24, 40.44, 35.36, 24.61, 23.20.

The mother liquor was evaporated to dryness to get 310 g of a red oily residue. This was dissolved in heptane (1 L) at 50° C., cooled down to 20° C. and filtered to get a second crop of compound 7 as a brown crystalline solid. Yield 2$^{nd}$ crop: 0.186 kg, 17%. NMR assay: 94% w/w. LC-MS method 1: 100% a/a. The structure of Compound 7 was proven by single crystal X-ray analysis. Compound 7 was processed to a crystalline intermediate with a residue of known chirality. X-ray crystal structure analysis of this intermediate allowed for the determination of the absolute configuration.

Example 2

Preparation of Compound 5 Using Method B

Scheme 2: Method B

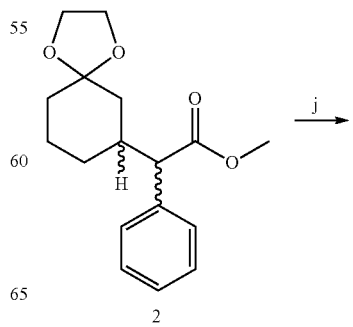

-continued

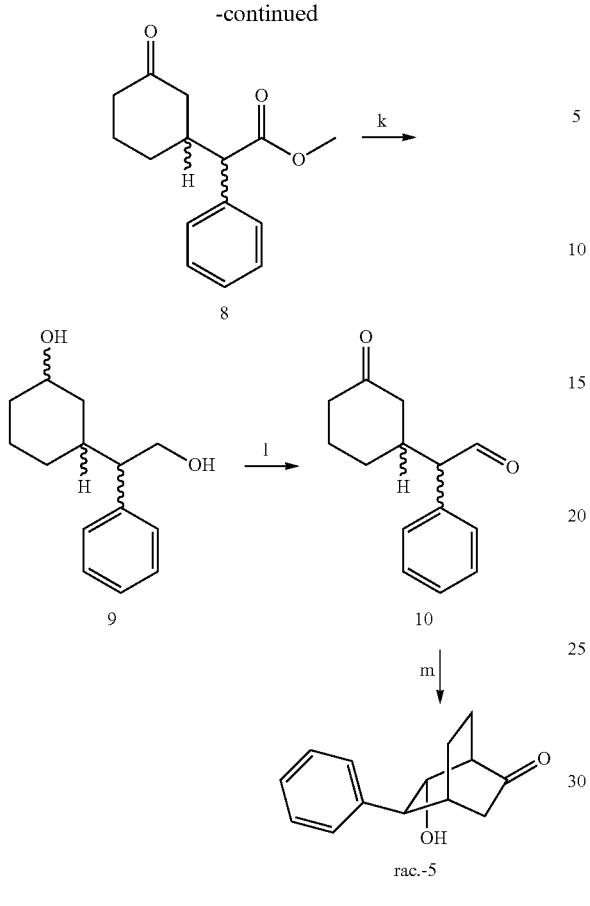

The following examples started from compound 2 which was derived from racemic compound 1.

Compound 8

Methyl 2-(3-oxocyclohexyl)-2-phenylacetate (mixture of stereoisomers)

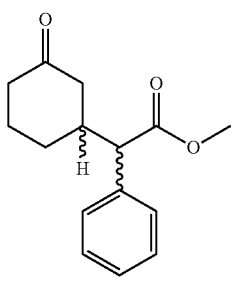 [SMILES: COC(=O)C(c1ccccc1)C1CCCC(=O)C1]

Compound 2 (2.8 g, mixture of stereoisomers) was dissolved in THF (10 mL). 15% HCl (10 mL) was added at 20-32° C. After 2 days stirring at r.t. water (50 mL) and DCM (50 mL) were added. After separation of the layers the aqu. phase was extracted with DCM (30 mL). The org. phase was dried over sodium sulphate, filtered over cotton and evaporated to dryness under reduced pressure to afford rac. compound 8 as a yellow oil which solidified at r.t. The solid was dissolved in TBME (10 mL) at 50° C. and the soln. cooled to 20° C. The suspension was filtered, the filter cake washed with TBME (20 mL) and the solid was dried under reduced pressure to afford rac. compound 8 as a white solid (first crop).

The mother liquor was evaporated to dryness under reduced pressure and the residue was suspended in heptane/TBME (1:2, 4 mL). After filtration and washing with heptane/TBME (1:2, 5 mL) the solid was further recrystallized from TBME (8 mL) to afford one single isomer of rac. compound 8 as second crop. Yield first crop: 0.4 g, 17% (1:1 mixture of diastereomers). LC-MS method 1: 100% a/a, $t_R$=1.51, 1.55 (1:1 mixture of diastereomers), $[M+1]^+$=247; GC-MS: 98% a/a, $t_R$=3.19, $[M+1]^+$=247; $^1$H-NMR (CDCl$_3$): δ=7.22-7.42 (m, 5H), 3.70 (s, 3H), 3.40 (d, J=10.4 Hz, 1H), 2.47-2.63 (m, 1H), 2.34-2.45 (m, 1H), 2.20-2.33 (m, 1H), 1.99-2.19 (m, 3H), 1.66-1.93 (m, 2H), 1.43-1.61 (m, 1H); $^{13}$C-NMR (CDCl$_3$): δ=210.17, 172.99, 136.72, 128.76, 128.45, 127.71, 57.74, 52.08, 46.44, 41.73, 41.19, 28.47, 24.49.

Yield second crop: 0.53 g, 22% (1 diastereomer). LC-MS method 1: 100% a/a, $t_R$=1.53, $[M+1]^+$=247; GC-MS: 99% a/a, $t_R$=3.19, $[M+1]^+$=247. $^{13}$C-NMR (CDCl$_3$): δ=210.17, 172.99, 136.72, 128.76, 128.45, 127.71, 57.74, 52.08, 46.44, 41.73, 41.19, 28.47, 24.49.

Compound 9

3-(2-Hydroxy-1-phenylethyl)cyclohexan-1-ol (mixture of stereoisomers)

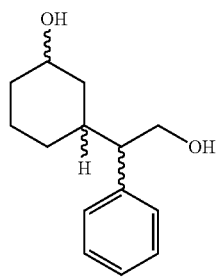 [SMILES: OCC(c1ccccc1)C1CCCC(O)C1]

A soln. of compound 8 (12.3 g) in toluene (25 mL) was added to a 2.4N soln. of lithium aluminum hydride (25.1 mL in THF) in toluene (20 mL) at 0-27° C. After 1 h stirring at 20-25° C. water (1 mL) was added at 23-33° C., followed by THF (3 mL), water (3 ml) and 15% NaOH soln. (1 mL). Celite (2.5 g) and charcoal (2.5 g) were added, the mixture was filtered and the filter cake was washed with THF (175 mL). The filtrate was concentrated to dryness under reduced pressure to afford compound 9 as a waxy solid which was engaged in the next step without further purification. Yield compound 9: 10.76 g, 97%. LC-MS method 1: 72% a/a, $t_R$=1.20, 1.29, 1.35 min (mixture of isomers), $[M-32+1]^+$=185; GC-MS: 95% a/a, $t_R$=3.2 min, $[M-32+1]^+$=185, $[M-18+1]^+$=203.

Compound 10

2-(3-Oxocyclohexyl)-2-phenylacetaldehyde (mixture of stereoisomers)

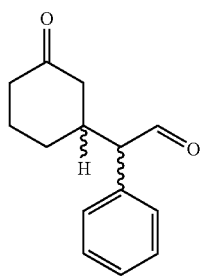

Compound 9 (2.0 g) was dissolved in EtOAc (10 mL). A soln. of KBr (0.11 g) in water (0.2 mL) and 2,2,6,6-tetramethylpiperidine-1-oxyl (0.01 g) were added. Then, a soln. of sodium hypochlorite (15%, 9.4 mL) in sat. aqu. NaHCO$_3$ (3.8 mL) was added at 3-6° C. After stirring at 20-25° C. for 16 h 2.75N sodium thiosulfate soln. (0.5 mL9 was added, followed by water (10 mL). The layers were separated and the aqu. phase was extracted with EtOAc (10 ml). The org. phase was evaporated to dryness under reduced pressure at 50° C. to afford rac. compound 10 as a yellow oil. The crude product was not purified, the quality was sufficient for the next step. Yield: 1.72 g, 88%. LC-MS method 1: 87% a/a, $t_R$=1.48, 1.51, 1.55 (11:31:58 mixture of diastereomers), [M−18+1]$^+$=199; GC-MS: 91% a/a, $t_R$=3.02, 3.06 (two diasteromers), [M+1]$^+$= 217.

Rac. Compound 5

(1R*,4R*,5S*,6S*)-6-Hydroxy-5-phenylbicyclo
[2.2.2]octan-2-one

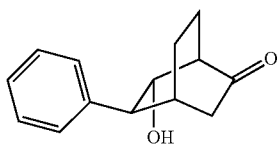 [SMILES: O=C1CC2CCC1C(O)C2c1ccccc1]

Compound 10 (1.68 g, mixture of stereoisomers) was dissolved in EtOAc (3.2 mL). After addition of 32% HCl (0.8 mL) the mixture was stirred at 55° C. ET for 1.5 h. The suspension was cooled to r.t. and EtOAc (15 mL) and ½-sat. aqu. NaHCO$_3$ soln. (20 mL) were added. After separation of the layers the org. phase was washed with water (20 mL) and solvent was removed under reduced pressure. TBME (10 mL) and heptane (20 mL) were added to the concentrated oil. The suspension was filtered and the crystals washed with heptane (10 mL) before drying at 50° C. under reduced pressure to afford rac. compound 5 as light-brown solid. Yield: 0.51 g, 30%. GC-MS: 95% a/a, $t_R$=3.30, [M+1]$^+$= 217, [M−18+1]$^+$=199; diastereomeric purity: >99%; $^1$H-NMR (CDCl$_3$): corresponds to compound 5, δ=7.33-7.43 (m, 4H), 7.20-7.33 (m, 1H), 4.34-4.69 (m, 1H), 2.92-2.98 (m, 1H), 2.68 (br. s, 1H), 2.57-2.62 (m, 1H), 2.47-2.56 (m, 1H), 2.30-2.44 (m, 2H), 1.84-1.95 (m, 2H), 1.70-1.82 (m, 1H), 1.33-1.52 (m, 1H).

Example 3

Preparation of Compound 5 Using Method C

Scheme 3: Method C

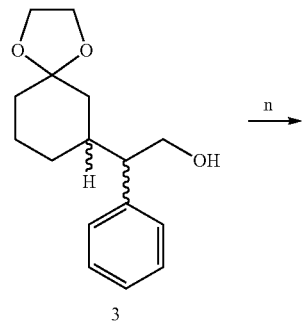

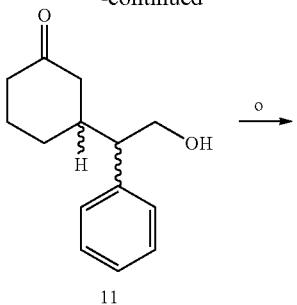

11

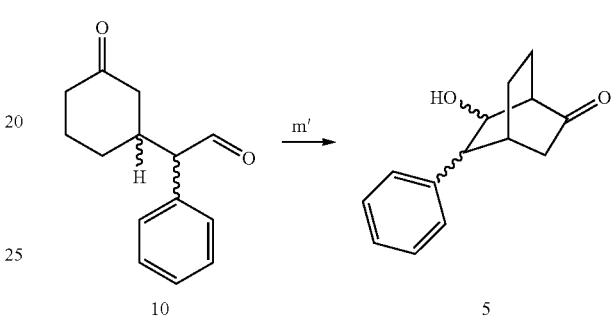

10    5

Compound 11

3-(2-Hydroxy-1-phenylethyl)cyclohexanone
(mixture of stereoisomers)

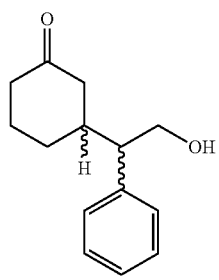 [SMILES: O=C1CCCC(C(CO)c2ccccc2)C1]

Compound 3 (20 g, mixture of stereoisomers) was dissolved in THF (100 mL). After addition of 25% HCl (20 mL) at 20-35° C. the yellow soln. was stirred for 24 h at r.t. The solvent was removed under reduced pressure and toluene (100 mL) and water (40 mL) were added. After phase separation the org. phase was evaporated to dryness under reduced pressure at 50° C. for 20 min. to yield 16.3 g of a yellow oil. The crude product was purified by chromatography on silica gel 60 (100 g) with a gradient from heptane to heptane/EtOAc 6:4 to afford compound 11 as a yellow oil which was used in the next step without further purification. Yield: 5.61 g, 34%. NMR assay: 93% w/w. LC-MS method 1: 94% a/a, $t_R$=1.16, 1.22, [M−18+1]$^+$=201; GC-MS: 100% a/a, $t_R$=1.16, 1.22, [M−18+1]=201; $^1$H-NMR (CDCl$_3$): δ=7.28-7.46 (m, 3H), 6.97-7.26 (m, 2H), 3.75-4.05 (m, 2H), 2.68-2.82 (m, 1H), 2.59-2.66 (m, 0.6H, isomer), 2.32-2.44 (m, 1H), 2.04-2.31 (m, 4H), 1.84-2.04 (m, 1H), 1.41-1.81 (m, 2H), 1.20-1.37 (m, 2H).

Compound 10

2-(3-Oxocyclohexyl)-2-phenylacetaldehyde (mixture of stereoisomers)

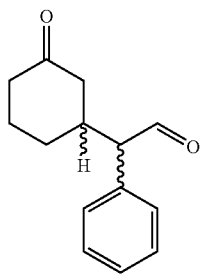 [SMILES: O=CC(c1ccccc1)C1CCCC(=O)C1]

Compound 11 (5.5 g, mixture of stereoisoemrs) was dissolved in DCM. A soln. of KBr (0.3 g) in water (0.66 mL) was added. After addition of 2,2,6,6-tetramethylpiperidine-1-oxyl (0.0394 g) at 0° C. a soln. of sodium hypochlorite (15.4 mL) in sodium bicarbonate (6.3 mL, pH soln. 8.63) was added at 5-15° C. Further sodium hypochlorite (1.55 mL) in NaHCO$_3$ (0.63 mL) was added at 5-15° C. after 2 h. After stirring for 1 h sodium 2.75N thiosulfate soln. (0.33 mL) was added, followed by water (20 mL). Phase separation ensued and the org. phase was concentrated to dryness under reduced pressure at 40° C. for 50 min to afford compound 10 as an orange oil. The crude product was not purified and used as is in the next step. Yield: 4.6 g, 84%. LC-MS method 1: 94% a/a, $t_R$=1.31, 1.35, [M−18+1]$^+$=199; GC-MS: 100% a/a, $t_R$=3.03, 3.06 (two diasteromers), [M+1]=217, [M−18+1]=199; $^1$H-NMR (CDCl$_3$,): δ=9.71-9.74 (m, 3 singulets, 3 isomers, 1H), 7.31-7.50 (m, 3H), 7.09-7.28 (m, 2H), 3.40-3.54 (m, 1H), 2.53-2.75 (m, 1.75H, isomer), 1.11-2.52 (m, 8H).

Rac. Compound 5

(1R*,4R*,5S*,6S*)-6-Hydroxy-5-phenylbicyclo [2.2.2]octan-2-one

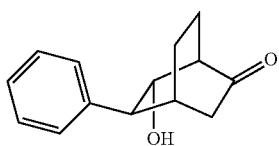 [SMILES: O=C1CC2CCC1C(O)C2c1ccccc1]

Compound 10 (0.38 g, mixture of isomers) in THF (8 mL) and 1N HCl (0.35 mL) was stirred at 75° C. for 3.5 h. Solvent was removed under reduced pressure and EtOAc (15 mL) and water (10 mL) were added. After phase separation the org. phase was dried over sodium sulphate and concentrated to dryness at 45° C. to afford compound 5 (mixture of steroisomers) as a brown foam. Yield: 0.38 g, 100%. LC-MS method 1: 90% a/a, $t_R$=1.22, [M−18+1]$^+$=199; GC-MS: 97% a/a, $t_R$=3.23, 3.29, 3.33 (27:61:11), [M+1]=217, [M−18+1]=199. The crude product can be subjected to the crystallization procedure as depicted for rac. compound 5 in Scheme 2, Method B, to obtain pure rac. compound 5 as colorless crystalline solid.

Example 4

Preparation of Compound 4 Using Method D

Scheme 4: Method D

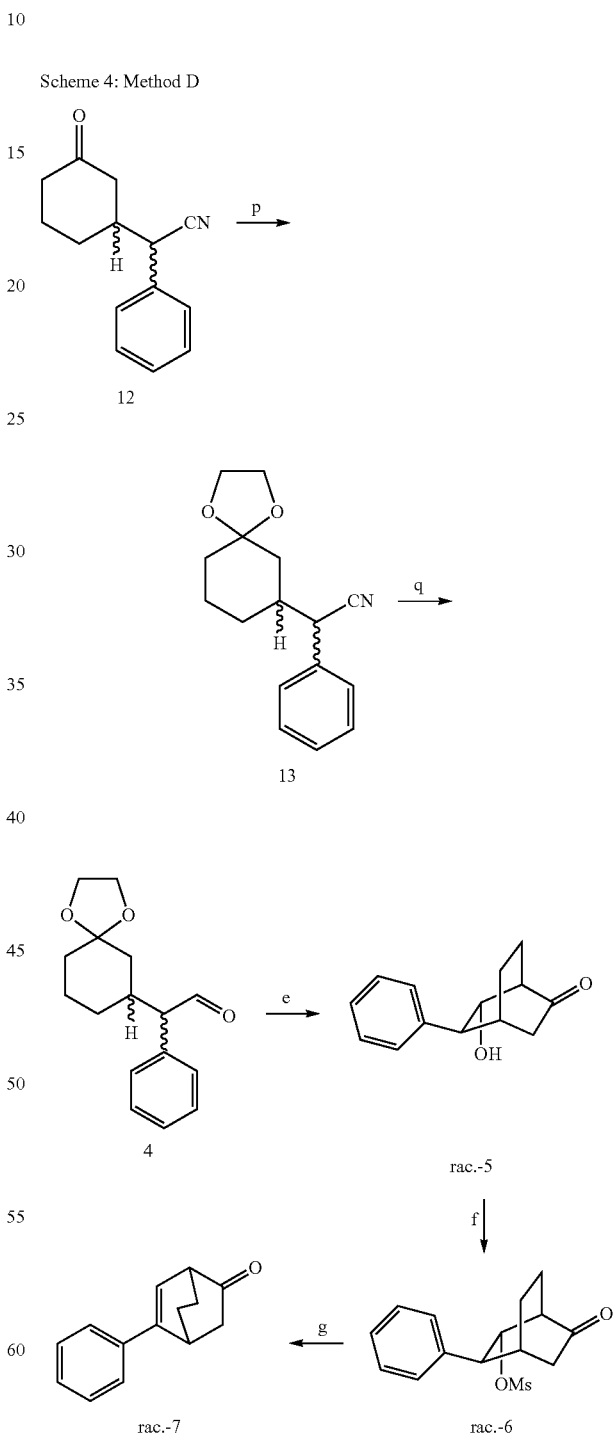

Compound 12 was prepared according to published procedures from cyclohexenone and phenylacetonitrile, see for instance: T. Strzalko, J. Seyden-Penne, L. Wartski, J. Corset, M. Castella-Ventura, F. Froment, *J. Org. Chem.* 1998, 63, 3295-3301.

Compound 13

2-Phenyl-2-(1,4-dioxaspiro[4.5]decan-7-yl)acetonitrile (mixture of stereoisomers)

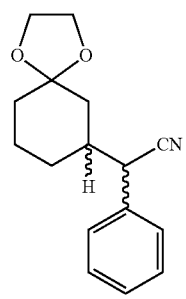 [SMILES: N#CC(c1ccccc1)C1CCCC2(C1)OCCO2]

To a soln. of compound 12 (10 g, 1:1 mixture of diastereoisomers) in toluene (40 mL) was added ethylene glycol (26 mL) and p-toluenesulfonic acid mono hydrate (0.5 g). The resulting mixture was heated to reflux for 1.5 h with azeotropical removal of water. It was then cooled down to r.t. A 1M aqu. soln. of NaOH (0.15 mL) was added. Water was added (40 mL) and the layers were separated. The org. layer was washed with water (40 mL) and concentrated to dryness at 45° C. under reduced pressure to yield rac. compound 12 as an orange oil containing traces of residual toluene which was used in the next step without further purification. Yield: 11.9 g, 99% (1:1 mixture of diastereomers). LC-MS method 2: 67% a/a (toluene substracted), $t_R$=1.50, $[M+1]^+$=258; GC-MS: 98% a/a, $t_R$=3.52, $[M+1]^+$=258; $^1$H-NMR (MeOD): δ=7.32-7.45 (m, 5H), 7.10-7.26 (m, 1H), 3.84-4.01 (m, 4H), 2.03-2.18 (m, 1H), 1.62-1.85 (m, 4H), 1.30-1.56 (m, 3H), 1.07-1.21 (m, 1H).

Compound 4

2-Phenyl-2-(1,4-dioxaspiro[4.5]decan-7-yl)acetaldehyde (mixture of stereoisomers)

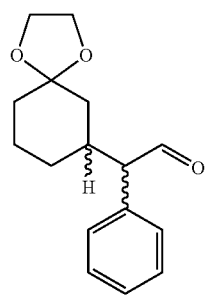 [SMILES: O=CC(c1ccccc1)C1CCCC2(C1)OCCO2]

To a 1M soln. of diisobutylaluminum hydride in heptane (542 mL) at r.t. was added dropwise a soln. of compound 13 (82 g, 1:1 mixture of diastereoisomers) in THF (82 mL) so that the temp. did not exceed 25° C. The resulting mixture was stirred at r.t. for 1 h. It was then cooled down to 5° C., TBME (575 mL) was added followed by the slow addition of a mixture of water (23 mL) in THF (115 mL). A soln. of citric acid monohydrate (134 g) in water (246 mL) was added dropwise and the resulting mixture was stirred for 1 h. The layers were separated and the aqu. phase was extracted with TBME (575 mL). The combined org. extracts were concentrated to dryness under reduced pressure at 45° C. to afford compound 4 as a yellow oil which was used in the next step without further purification. Yield: 49 g, 59% (1:1 mixture of diastereomers). LC-MS method 2: 84% a/a, $t_R$=1.24, 1.29, $[M-18]^+$=242; $^1$H-NMR (CD$_3$OD): δ=9.67 (s, 0.5H), 9.66 (s, 0.5H), 7.44-7.16 (m, 5H), 3.37-4.07 (m, 4H), 2.41-2.65 (m, 1H), 0.77-1.92 (m, 9H).

Rac. Compound 5

(1R*,4R*,5S*,6S*)-6-Hydroxy-5-phenylbicyclo[2.2.2]octan-2-one

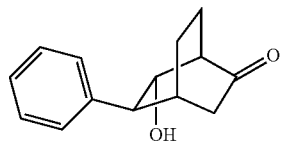 [SMILES: O=C1CC2CCC1C(O)C2c1ccccc1]

To a soln. of compound 4 (186 g, 1:1 mixture of diastereomers) in THF (930 mL) at r.t. was added a 5M aqueous soln. of phosphoric acid (930 mL). The mixture was heated to 80° C. for 5 h. The volatiles were removed under vacuum at 45° C. iPrOAc (1300 mL) and water (1300 mL) were added. The layers were separated and the organic layer was washed with water (930 mL). The combined organic extracts were concentrated at 45° C. under reduced pressure to afford rac. compound 5 as a crude orange solid which was used in the next step without further purification. Yield: 155 g (crude yield), 101%. LC-MS method 2: 83% a/a, $t_R$=0.96. $^1$H-NMR (CDCl$_3$): corresponds to rac. compound 5. The crude product can be subjected to the crystallization procedure as depicted for compound 5 to obtain pure rac. compound 5 as colourless crystalline solid with diastereomeric purity>99%.

Rac. Compound 6

(1R*,2S*,3S*,4R*)-6-oxo-3-phenylbicyclo[2.2.2]octan-2-yl methanesulfonate

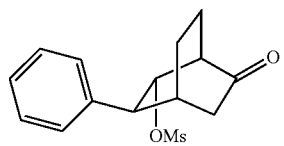 [SMILES: CS(=O)(=O)OC1C2CCC(CC2=O)C1c1ccccc1]

Rac. compound 5 (171 g) was dissolved in DCM (1200 mL) followed by triethylamine (221 mL). The suspension was cooled to 0° C. and methane sulfonyl chloride (11.6 mL) was added at 10-20° C. After 1 h, the mixture was concentrated to dryness. The residue was taken up in iPrOAc (1 L) and water (1 L). The layers were separated and the aqueous phase was extracted with iPrOAc (500 mL). The combined org. extracts were concentrated under reduced pressure to yield rac. compound 6 as a brown oil which was used in the next step without further purification. Yield: 208 g (crude yield), 89%. LC-MS method 2: 70% a/a, $t_R$=1.1. $^1$H-NMR (CDCl$_3$): corresponds to compound 6.

Rac Compound 7

(1R*,4R*)-5-phenylbicyclo[2.2.2]oct-5-en-2-one

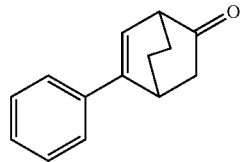 [SMILES: O=C1CC2CCC1C=C2c1ccccc1]

A soln. of rac. compound 6 (190 g) in DMF (380 mL) was added at r.t. to a suspension of LiBr (56 g) and Li$_2$CO$_3$ (48 g) in DMF (570 mL). The resulting mixture was heated to 150° C. for 1 h. It was cooled down to r.t. Water (1300 mL) and iPrOAc (1300 mL) were added and the layers were separated. The organic layer was washed with brine (1300 mL), water (1300 mL) and concentrated to dryness under vacuum at 50° C. to yield rac. compound 7. Yield: 117 g (crude yield), 91%. 108 g of this crude product was purified by short-path distillation at 120° C. and 0.001 mbar to yield 47 g (37%) of rac compound 7. LC-MS method 2: 97% a/a, $t_R$=1.26. $^1$H-NMR (CD$_3$OD): δ=corresponds to rac. compound 7.

The invention claimed is:

1. A process for the synthesis of 6-hydroxy-5-arylbicyclo[2.2.2]octan-2-one compounds, the compounds of the formula (II):

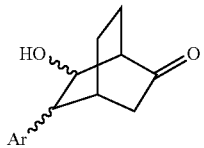

Formula (II)

wherein the compound of formula (II) is formed in a reaction mixture in diastereomerically enriched form; wherein the major diastereoisomer is (1R*,4R*,5S*,6S*)-6-hydroxy-5-arylbicyclo[2.2.2]octan-2-one:

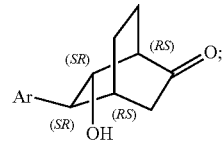

said process comprising a cyclization of a compound of formula 4:

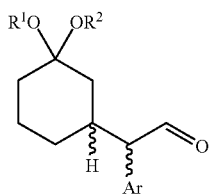

Formula 4 wherein

Ar represents an aryl group; and

—OR$^1$ and —OR$^2$, together with the carbon atom to which they are attached, represent a ketal group;

wherein said cyclization is performed in presence of:

an aqueous mineral acid; and a solvent; wherein said solvent is present in an amount of about 1-10 vol. with respect to the compound of formula 4; and wherein said compound of formula (II) is isolated from the reaction mixture by solid-liquid separation.

2. The process according to claim 1, wherein said compound of formula 4, is obtained from a compound of formula 2:

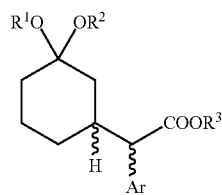

Formula 2 wherein

Ar represents an aryl group;

—OR$^1$ and —OR$^2$, together with the carbon atom to which they are attached to, represent a ketal group; and —COOR$^3$ represents an ester group.

3. The process according to claim 2, wherein said compound of formula 4 is obtained from said compound of formula 2 via a direct reduction of the ester group —COOR$^3$, or, via a sequence of reaction steps comprising first a reduction of the ester group —COOR$^3$ of the compound of formula 2 to the corresponding alcohol of formula 3:

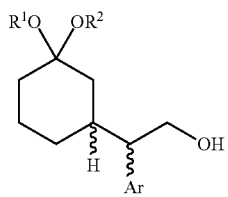

Formula 3 and a subsequent oxidation of said alcohol.

4. The process according to claim 2, wherein said compound of formula 2:

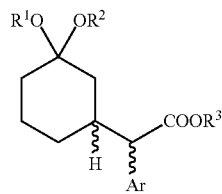

Formula 2 is obtained by a transition metal-catalyzed alpha-arylation of a carbonyl-containing compound of formula 1:

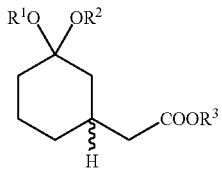

Formula 1 wherein

Ar represents an aryl group;

—OR¹ and —OR², together with the carbon atom to which they are attached to, represent a ketal group; and —COOR³ represents an ester group.

5. The process according to claim 4, wherein the compound of formula 1 is used in enantiomerically enriched form.

6. The process according to claim 1, wherein the compound of the formula (II) is further transformed to a compound the formula (I):

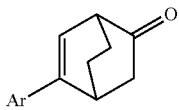

Formula (I)

wherein said transformation of the compound of the formula (II) to the compound of the formula (I) is effected via an elimination step.

7. The process according to claim 6, wherein the compound of formula 6:

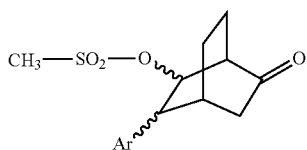

Formula 6 is an intermediate of said elimination step.

8. A compound of the formula 4:

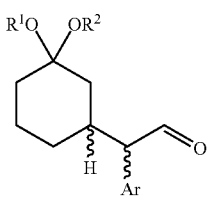

Formula 4 wherein

Ar represents an aryl group; and

—OR¹ and —OR², together with the carbon atom to which they are attached to, represent a ketal group.

9. The compound according to claim 8 selected from the group consisting of:

2-Phenyl-2-((R)-1,4-dioxaspiro[4.5]decan-7-yl)-acetaldehyde; and

2-Phenyl-2-(1,4-dioxaspiro[4.5]decan-7-yl)-acetaldehyde.

10. A compound of the formula 3:

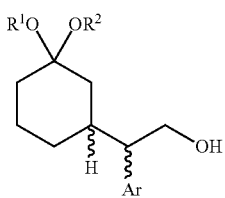

Formula 3 wherein

Ar represents an aryl group; and

—OR¹ and —OR², together with the carbon atom to which they are attached to, represent a ketal group.

11. The compound according to claim 10 selected from the group consisting of:

2-Phenyl-2-((R)-1,4-dioxaspiro[4.5]decan-7-yl)-ethanol;

2-Phenyl-2-(1,4-dioxaspiro[4.5]decan-7-yl)-ethanol;

rac-(R*)-2-Phenyl-2-((R*)-1,4-dioxaspiro[4.5]decan-7-yl)-ethanol; and rac-(R*)-2-Phenyl-2-((S*)-1,4-dioxaspiro[4.5]decan-7-yl)-ethanol.

12. A compound of the formula 2:

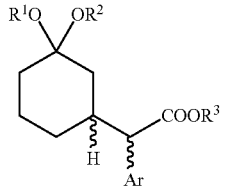

Formula 2 wherein

Ar represents an aryl group;

—OR¹ and —OR², together with the carbon atom to which they are attached to, represent a ketal group; and —COOR³ represents an ester group.

13. The compound according to claim 12 selected from the group consisting of:

Methyl 2-phenyl-2-((R)-1,4-dioxaspiro[4.5]decan-7-yl)-acetate;

Methyl 2-phenyl-2-(1,4-dioxaspiro[4.5]decan-7-yl)-acetate;

rac-(R*)-Methyl 2-phenyl-2-((R*)-1,4-dioxaspiro[4.5]decan-7-yl)-acetate; and rac-(R*)-Methyl 2-phenyl-2-((S*)-1,4-dioxaspiro[4.5]decan-7-yl)-acetate.

14. A compound of the formula 6:

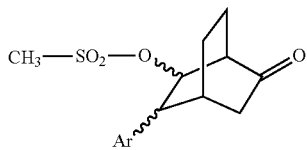

Formula 6 wherein
Ar represents an aryl group.

15. The compound according to claim 14 selected from the group consisting of:
(1R,2S,3S,4R)-6-oxo-3-phenylbicyclo[2.2.2]octan-2-yl methanesulfonate; and
rac-(1S*,2R*,3R*,4S*)-6-oxo-3-phenylbicyclo[2.2.2]octan-2-yl methanesulfonate.

16. The process according to claim 3, wherein said compound of formula 2:

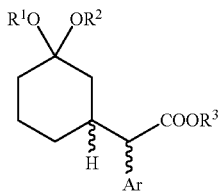

Formula 2 is obtained by a transition metal-catalyzed alpha-arylation of a carbonyl-containing compound of formula 1:

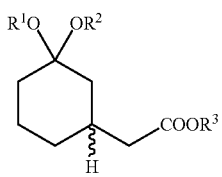

Formula 1 wherein
Ar represents an aryl group;
—$OR^1$ and —$OR^2$, together with the carbon atom to which they are attached to, represent a ketal group; and
—$COOR^3$ represents an ester group.

17. The process according to claim 2, wherein the compound of the formula (II) is further transformed to a compound the formula (I):

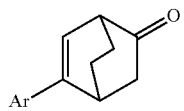

Formula (I)

wherein said transformation of the compound of the formula (II) to the compound of the formula (I) is effected via an elimination step.

18. The process according to claim 6, wherein the compound of the formula (I) wherein in this particular case Ar represents phenyl, is further transformed to any one of the following compounds:

rac-isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester, isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester; or isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester.

* * * * *

UNITED STATES PATENT AND TRADEMARK OFFICE
CERTIFICATE OF CORRECTION

PATENT NO. : 9,296,673 B2  
APPLICATION NO. : 13/880520  
DATED : March 29, 2016  
INVENTOR(S) : Abele et al.

It is certified that error appears in the above-identified patent and that said Letters Patent is hereby corrected as shown below:

In the Specification

Column 4, lines 1-8, in the structure for Formula IIa, the chirality labels "SR" should be "S"; and the chirality labels "RS" should be "R".

In the Claims

Column 52, line 14, claim 2, "," before "formula 4" should be deleted.

Column 52, line 31, claim 2, "to which they are attached to" should be "to which they are attached".

Column 53, line 18, claim 4, "to which they are attached to" should be "to which they are attached".

Column 53, line 24, claim 6, "compound the formula" should be "compound of the formula".

Column 53, line 67, claim 8, "to which they are attached to" should be "to which they are attached".

Column 54, line 25, claim 10, "to which they are attached to" should be "to which they are attached".

Column 54, line 54, claim 12, "to which they are attached to" should be "to which they are attached".

Column 56, line 5, claim 16, "to which they are attached to" should be "to which they are attached".

Column 56, line 10, claim 17, "compound the formula" should be "compound of the formula".

Signed and Sealed this  
Thirty-first Day of May, 2016

Michelle K. Lee  
*Director of the United States Patent and Trademark Office*